United States Patent
Shao et al.

(10) Patent No.: US 7,189,509 B2
(45) Date of Patent: Mar. 13, 2007

(54) ANALYSIS OF GENE EXPRESSION PROFILES USING SEQUENTIAL HYBRIDIZATION

(75) Inventors: Zhifeng Shao, 3145 Martin Kings Rd., Charlottesville, VA (US) 22902; Sitong Sheng, Charlottesville, VA (US); Shoudan Liang, 280 Parkside Dr., Palo Alto, CA (US) 94306

(73) Assignees: Zhifeng Shao, Charlottesville, VA (US); Siton Sheng, Charlottesville, VA (US); Shoudan Liang, Palo Alto, CA (US)

( * ) Notice: Subject to any disclaimer, the term of this patent is extended or adjusted under 35 U.S.C. 154(b) by 553 days.

(21) Appl. No.: 10/222,459

(22) Filed: Aug. 16, 2002

(65) Prior Publication Data

US 2003/0087279 A1    May 8, 2003

Related U.S. Application Data

(60) Provisional application No. 60/312,696, filed on Aug. 16, 2001.

(51) Int. Cl.
    *C12Q 1/68* (2006.01)
(52) U.S. Cl. .......................................... 435/6
(58) Field of Classification Search ...................... None
    See application file for complete search history.

(56) References Cited

U.S. PATENT DOCUMENTS

| | | | |
|---|---|---|---|
| 4,542,102 A | 9/1985 | Dattagupta et al. | 435/6 |
| 4,588,682 A | 5/1986 | Groet et al. | 435/6 |
| 4,670,380 A | 6/1987 | Dattagupta | 435/6 |
| 4,787,963 A | 11/1988 | MacConnell | 204/180.1 |
| 4,888,278 A | 12/1989 | Singer et al. | 435/6 |
| 5,215,882 A | 6/1993 | Bahl et al. | 435/6 |
| 5,514,545 A | 5/1996 | Eberwine | 435/6 |
| 5,589,335 A | 12/1996 | Kearney et al. | 435/6 |
| 5,665,540 A | 9/1997 | Lebo | 435/6 |
| 5,728,527 A | 3/1998 | Singer et al. | 435/6 |
| 5,759,777 A | 6/1998 | Kearney et al. | 435/6 |

(Continued)

OTHER PUBLICATIONS

Soker et al. Cell vol. 92:735-745. 1998.*
Amersham Biosciences. p. 1 2001.*
Vertegaal et al. FEBS Letters vol. 487:151-155. 2000.*
Schena et al. Science vol. 270:467-470.*
Mazzola et al. Biophysical Journal vol. 76:2922-2933. 1999.*
Brail et al. Mutation Research Genomics vol. 406:45-54. 1999.*
Amasino. "Accelreation of Nucleic Acid Hybridization Rate by Polyethylene Glycol" Anal. Biochem. 152:304-7 (1986).
Casey and Davidson. "Rates of Formation and Thermal Stabilities of RNA:DNA and DNA:DNA Duplexes at High Concentrations of Formamide" Nucleic Acids Res. 4:1539-52 (1977).
Chang et al. "Effects of Microscopic and Macroscopic Viscosity on the Rate of Renaturation of DNA" Biopolymers 13:1847-1858 (1974).
Flavell et al. "DNA-DNA Hybridization on Nitrocellulose Filters. 1. General Considerations and Non-Ideal Kinetics" Eur. J. Biochem. 47:535-43 (1974).
Forster et al. "Non-Radioactive Hybridization Probes Prepared by the Chemical Labelling of DNA and RNA with a Novel Reagent, Photobiotin" Nucleic Acids Res. 13:745-61 (1985).
Hoeltke et al. "Multiple Nucleic Acid Labeling and Rainbow Detection" Anal. Biochem. 207:24-31 (1992).
Hutton. "Renaturation Kinetics and Thermal Stability of DNA in Aqueous Solutions of Formamide and Urea" Nucleic Acids Res. 4:3537-55 (1977).
Jacobs et al. "The Thermal Stability of Oligonucleotide Duplexes is Sequence Independent in Tetraalkylammonium Salt Solutions: Application to Identifying Recombinant DNA Clones" Nucleic Acids Res. 16:4637-50 (1988).
Langer et al. "Enzymatic Synthesis of Biotin-Labeled Polynucleotides: Novel Nucleic Acid Affinity Probes" Proc. Natl. Acad. Sci. USA 78:6633-7 (1981).
Maskos and Southern. "Oligonucleotide Hybridizations on Glass Supports: A Novel Linker for Oligonucleotide Synthesis and Hybridization Properties of Oligonucleotides Synthesized In Situ" Nucleic Acids Res. 20:1679-84 (1992).
Renz and Kurz. "A Colorimetric Method for DNA Hybridization" Nucleic Acids Res. 12:3435-44 (1984).
Southern. "Detection of Specific Sequences Among DNA Fragments Separated by Gel Electrophoresis" J. Mol. Biol. 98:503-17 (1975).
Wahl et al. "Efficient Transfer of Large DNA Fragments frm Agarose Gels to Diazobenzyloxymethyl-Paper and Rapid Hybridization by Using Dextran Sulfate" Proc. Natl. Acad. Sci. USA 76:3683-7 (1979).
Wetmur and Davidson. "Kinetics of Renaturation of DNA" J. Mol. Biol. 31:349-370 (1968).
Wood et al. "Base Composition-Independent Hybridization in Tetramethylammonium Chloride: A Method for Oligonucleotide Screening of Highly Complex Gene Libraries" Proc. Natl. Acad. Sci USA 82:1585-8 (1985).

*Primary Examiner*—Gary Benzion
*Assistant Examiner*—Heather G. Calamita
(74) *Attorney, Agent, or Firm*—Morrison & Foerster LLP

(57) ABSTRACT

This invention relates generally to analysis of gene expression profiles. In particular, the present invention provides a method for a method for analyzing gene expression profiles of a cell, which method comprises: a) providing for isolated mRNA or cDNA target sequences from a cell; b) sequentially hybridizing said isolated mRNA or cDNA target sequences with a plurality of nucleotide probes; and c) assessing the sequential hybridization between said isolated mRNA or cDNA target sequences and said plurality of nucleotide probes to analyze gene expression profiles of said cell. Systems for analyzing gene expression profiles are also provided. Optical devices for detecting hybridization signal are further provided.

67 Claims, 13 Drawing Sheets

U.S. PATENT DOCUMENTS

| | | |
|---|---|---|
| 5,780,227 A | 7/1998 | Sheridan et al. ............... 435/6 |
| 5,837,836 A | 11/1998 | Friderici et al. ........... 536/23.1 |
| 5,853,986 A | 12/1998 | Petrie, III et al. .............. 435/6 |
| 5,932,451 A | 8/1999 | Wang et al. ............. 435/91.21 |
| 6,046,006 A | 4/2000 | Einsele et al. ................. 435/6 |
| 6,132,997 A | 10/2000 | Shannon ................. 435/91.21 |
| 6,200,752 B1 | 3/2001 | Lakowicz ...................... 435/6 |
| 6,210,932 B1 | 4/2001 | Teoule et al. ............. 435/91.1 |
| 6,225,077 B1 | 5/2001 | Schmidt et al. ............... 435/19 |
| 6,228,580 B1 | 5/2001 | Blumenfeld et al. ........... 435/6 |
| 6,235,483 B1 | 5/2001 | Wolber et al. ................. 435/6 |
| 6,248,525 B1 | 6/2001 | Nilsen ........................... 435/6 |
| 6,255,105 B1 | 7/2001 | Marchetti et al. ........... 435/325 |
| 6,258,536 B1 | 7/2001 | Oliner et al. ................... 435/6 |
| 6,268,147 B1 | 7/2001 | Beattie et al. ................. 435/6 |
| 6,303,301 B1 | 10/2001 | Mack ............................ 435/6 |
| 6,309,824 B1 | 10/2001 | Drmanac ....................... 435/6 |
| 6,344,316 B1 | 2/2002 | Lockhart et al. ............... 435/6 |
| 6,355,429 B1 | 3/2002 | Nygren et al. ................. 435/6 |
| 6,376,177 B1 | 4/2002 | Poponin ........................ 435/6 |
| 6,379,898 B2 | 4/2002 | Shultz et al. .................. 435/6 |
| 6,403,957 B1 | 6/2002 | Fodor et al. ................ 250/302 |
| 6,410,229 B1 | 6/2002 | Lockhart et al. ............... 435/6 |
| 6,441,269 B1 | 8/2002 | Serafini et al. ............... 800/18 |
| 2003/0087265 A1* | 5/2003 | Sauter et al. .................. 435/6 |

* cited by examiner

Stage (A) Obtaining material
    Method 1. In situ extraction of cellular content

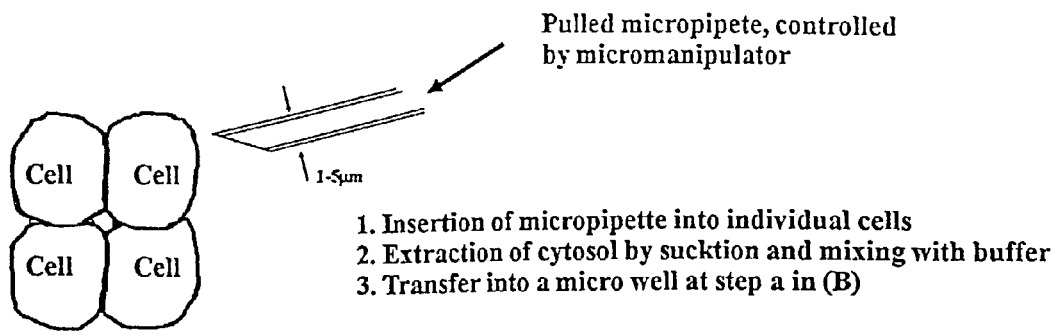

1. Insertion of micropipette into individual cells
    2. Extraction of cytosol by sucktion and mixing with buffer
    3. Transfer into a micro well at step a in (B)

Method 2. Release cellular content in micro well
        1. Isolate individual cells by microdissection, or flowcytometry
        2. Pick up wiht a micropipette by sucktion
        3. Release into micro well at step a in (B)

Figure 2A

Stage (B) Extraction, isolation, and immobilization of mRNA, cDNA

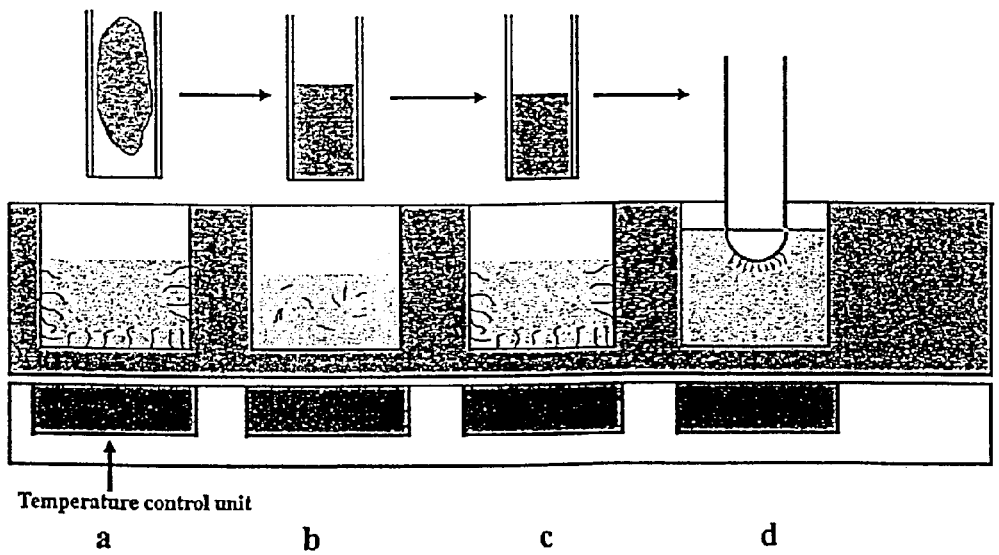

Figure 2B

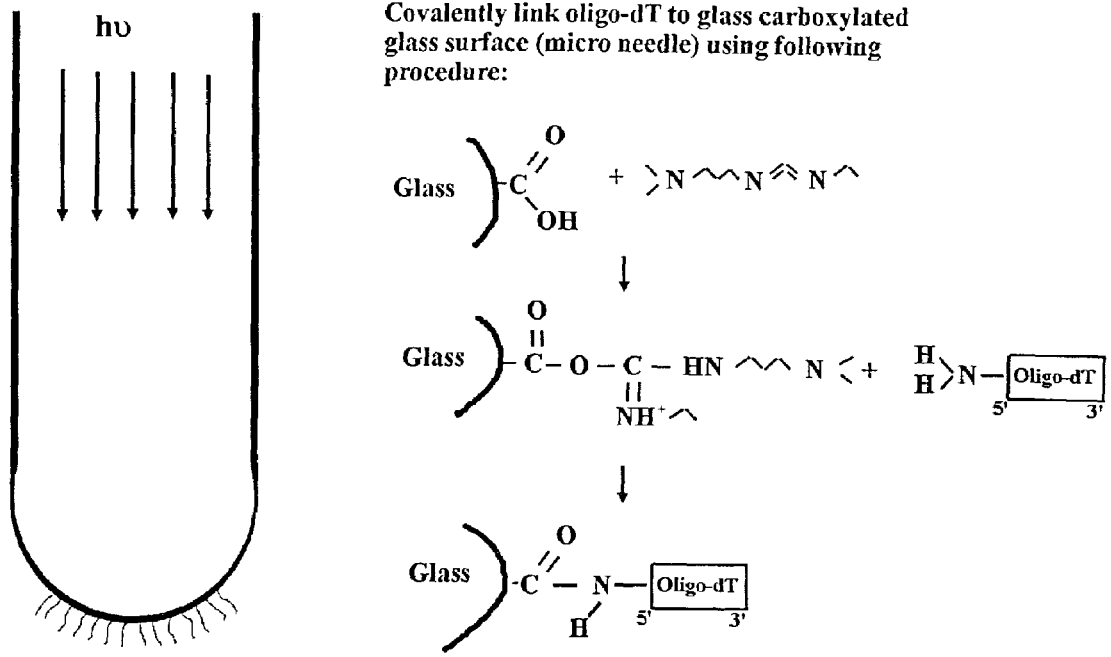
"∫" : Oligo-dT (15-40); Oligo-dA (15-40) sequences covalently linked on glass/quartz surface
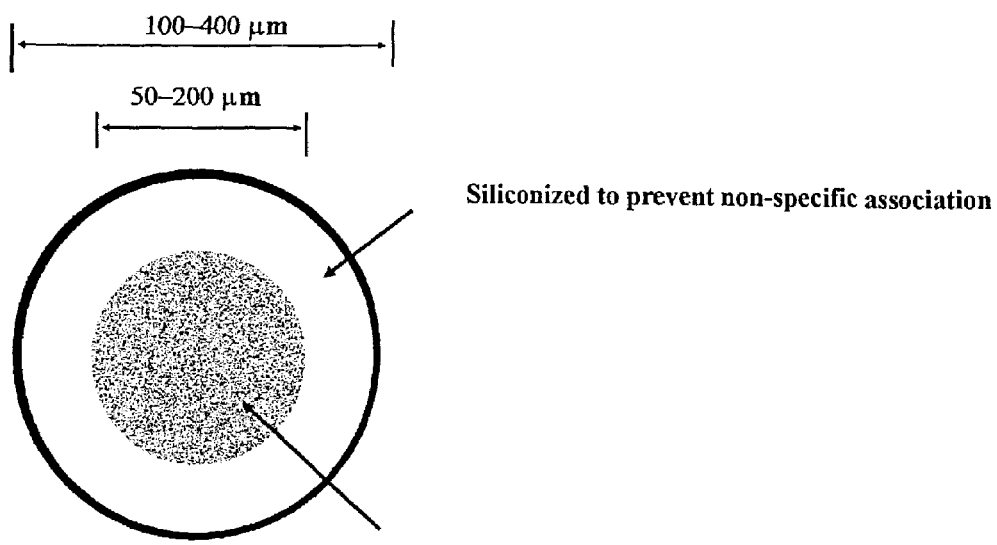
Covalently linked with oligo-dT, oligo-dA squences (tne area can be any shape other than circular as shown here)
Figure 4

1. synthesize short oligonucleotide sequences incorporated with one fluorescent nucleotide

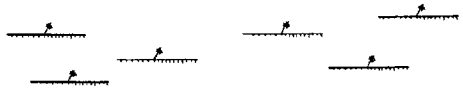

2. generate complimentary single stranded DNA to all short sequences

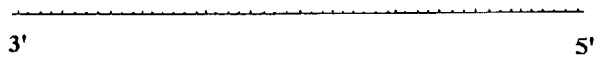

3. anneal short sequences to single stranded DNA

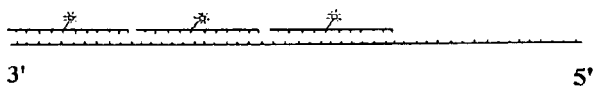

4. ligate the short single strand sequences to form double stranded DNA with fixed number of fluorophors and crosslink the double strand

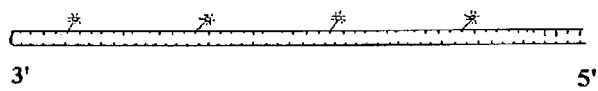

5. ligate, or crosslink to synthesized hybridization probe

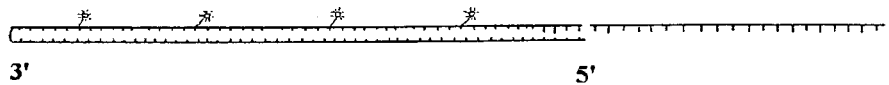

Characteristics of this synthesis procedure:
* Each fluorophor is about 20 bp away to eliminate self quenching effect
* Total of 15 fluorophors in the double stranded DNA to maximize signal without affecting hybridization
* All hybridization probe is tagged with a uniromly labeled fragment

Figure 5 ss-DNA stability

ANALYSIS OF GENE EXPRESSION PROFILES USING SEQUENTIAL HYBRIDIZATION

CROSS-REFERENCE TO RELATED APPLICATIONS

This application claims priority benefit of U.S. Provisional Application Ser. No. 60/312,696, filed Aug. 16, 2001, the content of which is incorporated by reference herein in its entirety.

STATEMENT REGARDING FEDERALLY SPONSORED RESEARCH OR DEVELOPMENT

The research and development described herein is at least partially supported by NIH R01 RR07720 and NSF DBI9730060. The United States Government may have certain rights in the inventions described and/or claimed herein.

TECHNICAL FIELD

This invention relates generally to analysis of gene expression profiles. In particular, the present invention provides a method for analyzing gene expression profiles of a cell, which method comprises: a) providing for isolated mRNA or cDNA target sequences from a cell; b) sequentially hybridizing said isolated mRNA or cDNA target sequences with a plurality of nucleotide probes; and c) assessing the sequential hybridization between said isolated mRNA or cDNA target sequences and said plurality of nucleotide probes to analyze gene expression profiles of said cell. Systems for analyzing gene expression profiles are also provided. Optical devices for detecting hybridization signal are further provided.

BACKGROUND OF THE INVENTION

The functional states and the specific genotype of a cell are predominantly determined by the set of genes expressed in that cell, not only by the number of genes but also by their relative level of expression. In general, both of these critical information can be obtained by an analysis of the level of messenger RNA (mRNA) expressed in the cell. An accurate characterization of the mRNA levels in various cells not only is necessary for a thorough understanding of the fundamental principles governing the determination of each cell type in the body, but can also be used to determine whether a cell has been transformed into a harmful, disease causing state.

Several different methods have been developed to quantify mRNA abundance in biological samples. But, so far, the most reliable, convenient and economical method for the quantitation of mRNA levels is based on the principle of hybridization, which uses target nucleic acid sequences to incubate with a probe sequence under conditions where the complementary probe and its target can form stable hybrid duplexes through base pairing, which is highly sequence specific. By measuring the hybridization results of probes to different mRNA or their cDNA, the expression level of each mRNA species in original sample can be quantified. Blot assays have been used for some time to hybridize nucleic acid material from biological samples to specifically designed probes for analyzing expression level of specific genes in the original sample. Although the traditional blot hybridization assays are well developed, it is not suitable for screening large number of genes and the sensitivity of this technique is relatively low, which requires a large amount of material. This technique further suffers from its low accuracy in quantitative analysis of expression profiles.

The more recent array technology, such as oligonucleotide array or cDNA array, is suited for the analysis of large number of genes, which is made possible by the use of parallel detection of hybridization signals. Both array methods involve physically immobilizing many different hybridization probes on a solid surface in a small array format. Target mRNA or cDNA in solution are hybridized with the tens of thousands different probes defined as "spots" on the surface. The amount of each target species is quantified by scanning individual "spot" in the whole array after targets have hybridized to the probes. This technology has been applied to both basic research and clinical applications. However, a major limitation of this approach is its need for large amount of target material, which is often impossible to obtain. In particular, it has been estimated that even under most ideal conditions, $10^6$–$10^7$ of cells would be required for an acceptable signal to noise ratio. The usefulness and the power of this approach notwithstanding, we must recognize that the ability of being able to analyze gene expression at large scale in single or just a few cells is an overwhelming need in both basic research in biology and clinical medicine. In fact, there are many important areas of application where the available materials for analysis cannot be more than a few cells. For example, to understand the principles governing the development of the embryo, we must be able to analyze the first differentiated cells that have a particular spatial relationship. Similarly, to understand how cancer is developed, it is preferable to analyze the early stages of the development, which may or may not exhibit identical traits as mature tumors. Even in the case of biopsy, the small amount of materials available makes it difficult to perform an in-depth analysis of the genes expressed that may be used as reliable markers for tumorigenesis. Therefore, the development of such a powerful technology for both fundamental research and medical diagnosis has constituted a major focus of biotechnology.

Although PCR amplification schemes have been employed to improve upon this lower limit, the large pools of target material generated by amplification have not been shown to faithfully represent the relative abundance of different targets in the original material, especially for those low copy number target species. Apparently, this technology is not applicable to single cell analysis with acceptable reliability. Furthermore, the accuracy of this method is also limited due to detection sensitivity.

A very important point to make, however, is the fact that in most practical applications, there is no need or even the desire to monitor the expression levels of the entire genome which involves hundreds of thousands of genes. Since usually there are up to few hundred genes involved in specific cellular pathways and certain disease such as hypertension, in which it is believed that there are about 150 target genes' expression are modified or changed, information related to these specific groups are of most interests. Another example is the prostate cancer where no more than 500 genes are believed to be involved in this disease.

To date, methods of analyzing gene expressions, which can be applied to single or a limited number of cells, employ fluorescence in situ hybridization, or hybridization based on reverse transcription coupled PCR (RT-PCR) using specific primers. In situ hybridization method has been used to directly visualize the expression of a few particular genes in individual cells, but the procedure involved is rather laborious and the sensitivity of this technique limited its application in gene species. Furthermore, the number of genes that can be analyzed in a sample is very limited. When the later RT-PCR based method is employed with specific primers for amplification, the complexity of the analysis limited the applicable number of genes, which is not realistic for monitoring expression profiles and quantifying the changes in expression levels.

In order to achieve the required sensitivity for single cell analysis and to be able to analyze a large number of genes, a different approach than the current array technology must be pursued. In this application, we describe a practical system and method thereof that is based on sequential detection of hybridization signals that not only is sufficiently sensitive for the analysis of mRNA levels from single cells, but can also allow the quantitation of up to several thousand gene products in a single analytical cycle. Therefore, the applicable range of this technology fulfills the gap between the array technology (suitable for hundreds of thousands of genes by parallel analysis) and the more conventional approaches (only adequate for analyzing small number of gene products). This technology will open the possibility to analyze groups of genes involved in specific pathways, such as development of the embryo and the neuro network, or processes involved in the development of certain diseases, such as hypertension, cancer, with minute amount of materials from few cells and even down to a single cell, as well as applications in clinical medicine, such as the detection of cancerous cells at an early few cell stage, and other genetically determined diseases.

BRIEF SUMMARY OF THE INVENTION

In one aspect, the present invention is directed to a method for analyzing gene expression profiles of a cell, which method comprises: a) providing for isolated mRNA or cDNA target sequences from a cell; b) sequentially hybridizing said isolated mRNA or cDNA target sequences with a plurality of nucleotide probes; and c) assessing the sequential hybridization between said isolated mRNA or cDNA target sequences and said plurality of nucleotide probes to analyze gene expression profiles of said cell.

In another aspect, the present invention is directed to a system for analyzing gene expression profiles of a cell, which system comprises: a) means for providing isolated mRNA or cDNA target sequences from a cell; b) means for sequentially hybridizing said isolated mRNA or cDNA target sequences with a plurality of nucleotide probes; and c) means for assessing the sequential hybridization between said isolated mRNA or cDNA target sequences and said plurality of nucleotide probes to analyze gene expression profiles of said cell.

In still another aspect, the present invention is directed to an optical device for detecting hybridization signal, which device comprises: a) a microneedle comprising a mRNA or cDNA target sequence immobilized on its tip and in optical connection with a light source; b) a light concentrator; c) a filter system; and d) a photomultiplier tube (PMT) unit, wherein in operation, hybridization of said mRNA or cDNA target sequence to a complementary probe brings a fluorescent label to the close proximity to said tip of said microneedle, provision of light to said tip from said light source generates fluorescent light from said tip, and said fluorescent light is reflected by said light concentrator to become parallel light passing through said filter system and detected by said PMT unit.

BRIEF DESCRIPTION OF THE SEVERAL VIEWS OF THE DRAWING(S)

FIG. 1 shows a block diagram of this method, illustrating the steps in realizing sequential gene expression analysis.

FIGS. 2A and 2B illustrate 2 stages in handling, extracting, and immobilizing mRNA, cDNA material from single or a small cluster of cells. The procedures referred to in FIG. 2B include: (a) Cell lysate of cellular extracts are transferred into a micro well, and mRNA are captured by oligo-dT sequences covalently linked to the wall, and then subsequently eluted. Alternately, cDNAs are synthesized with oligo-dT primer. Using covalently linked first strand cDNAs as templates, second strand cDNAs are synthesized for the use as target sequences; (b) mRNA eluted from step (a) can be reverse transcribed into first strand cDNA with oligo-dT primer; (c) Using micro well coated with selected complimentary sequences to hybridize with mRNA or cDNA, unwanted species are removed from the total population; and (d) Hybridize mRNA, second strand cDNA, or first strand cDNA to oligo-dT or oligo-dA sequences linked on the micro probe (needle), cDNA is synthesized with oligo-dT as the primer or crosslinked to oligo-dA to achieve immobilization.

FIG. 4 shows an illustration for the design of the microneedle used for immobilizing the target sequences, and the chemistry of covalently linking oligonucleotide sequences to the surface of the needle.

FIG. 5 shows an example of synthesizing a uniform fluorescent label with fixed number of fluorophors and tagging the hybridization probe with this label.

Figure 6:
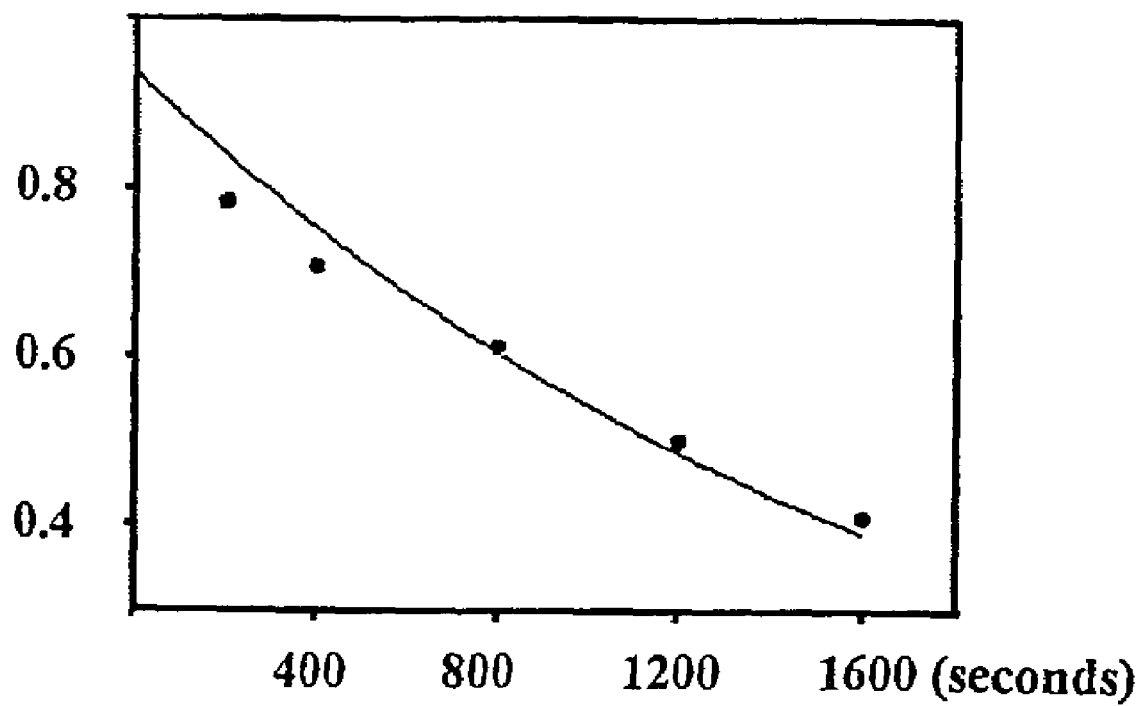

FIG. 6 shows a plot of hybridization kinetics of bead immobilized oligo-dT sequence and poly-dA tailed single strand DNA sequence. In this case, the probe is in vast excess of the target. Therefore, the process becomes first order.

Figure 7A:
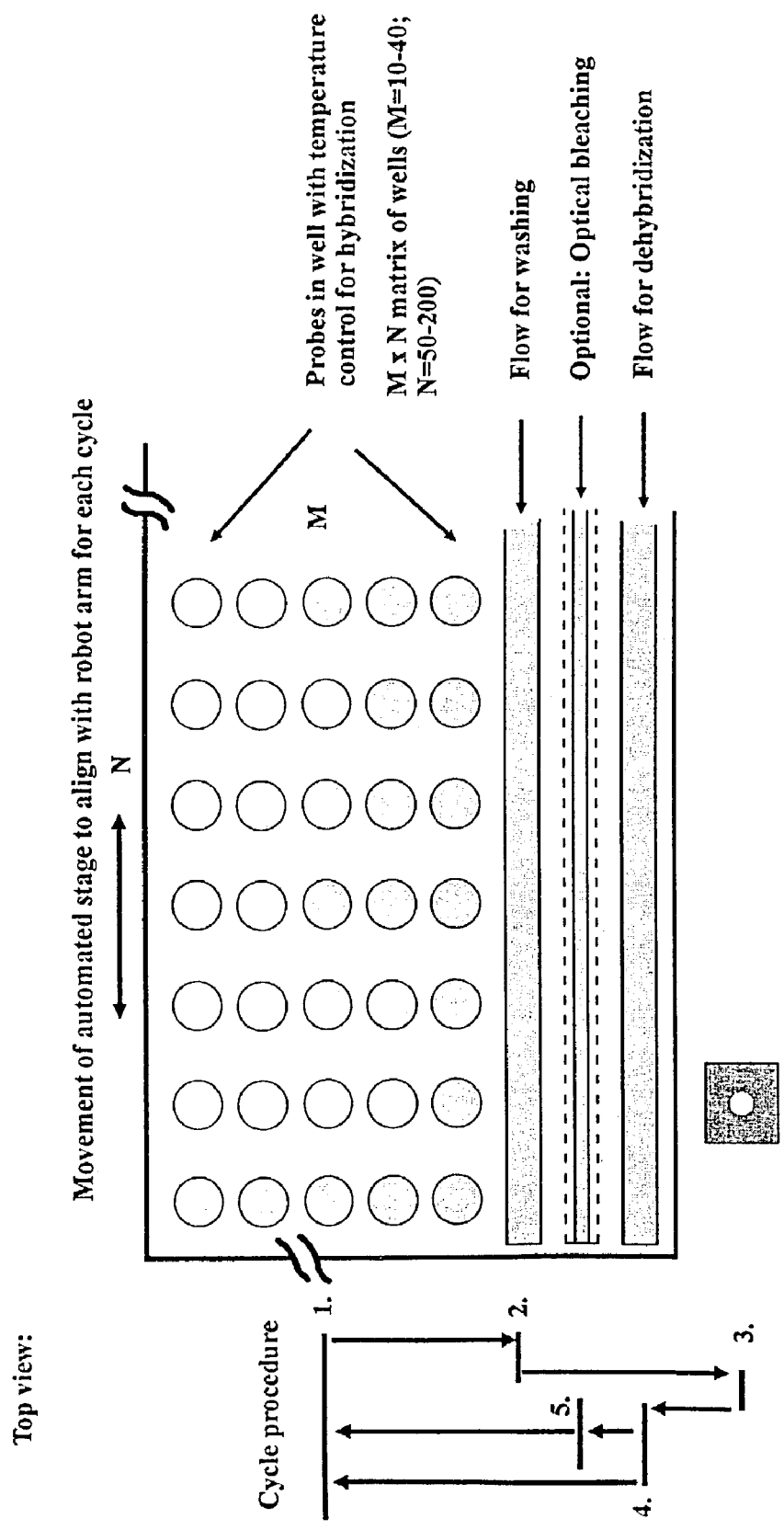
Figure 7B:
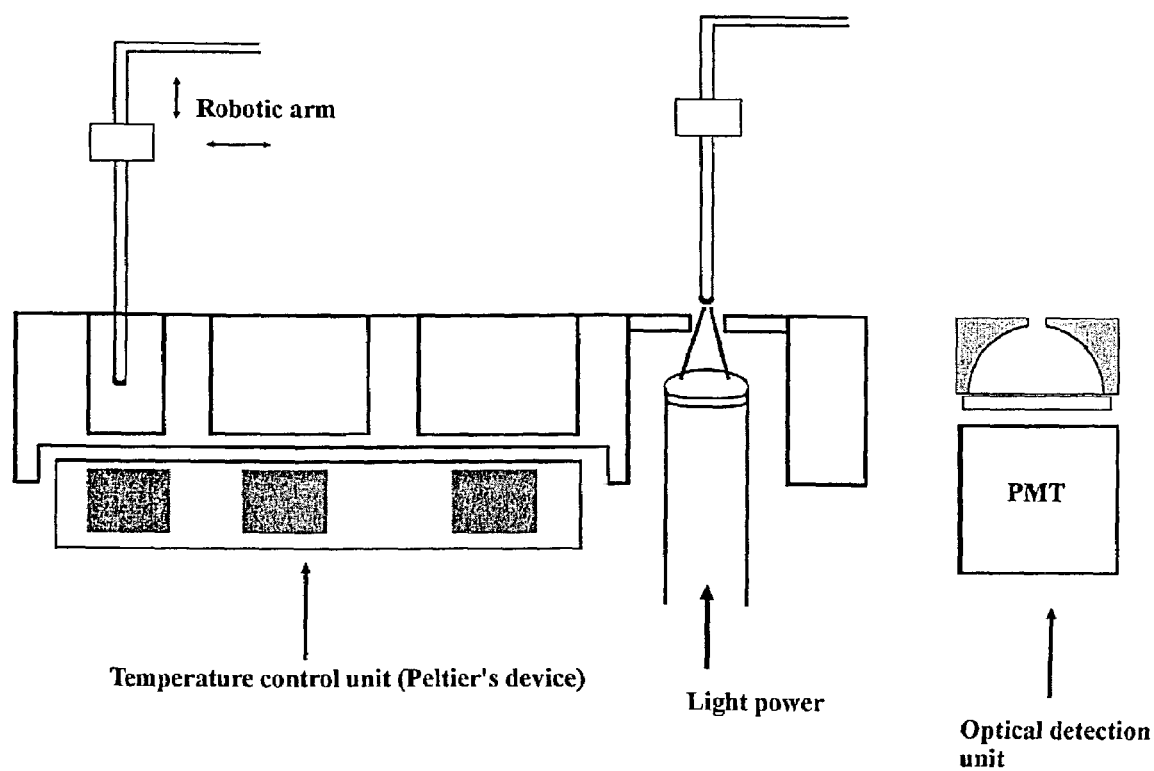

FIG. 7 illustrates a representative hybridization station for the analytical cycle. The probes are contained in the "matrix" and the entire gene group is pre-fabricated precisely to allow an automated analysis with robotic control.

Figure 8A:
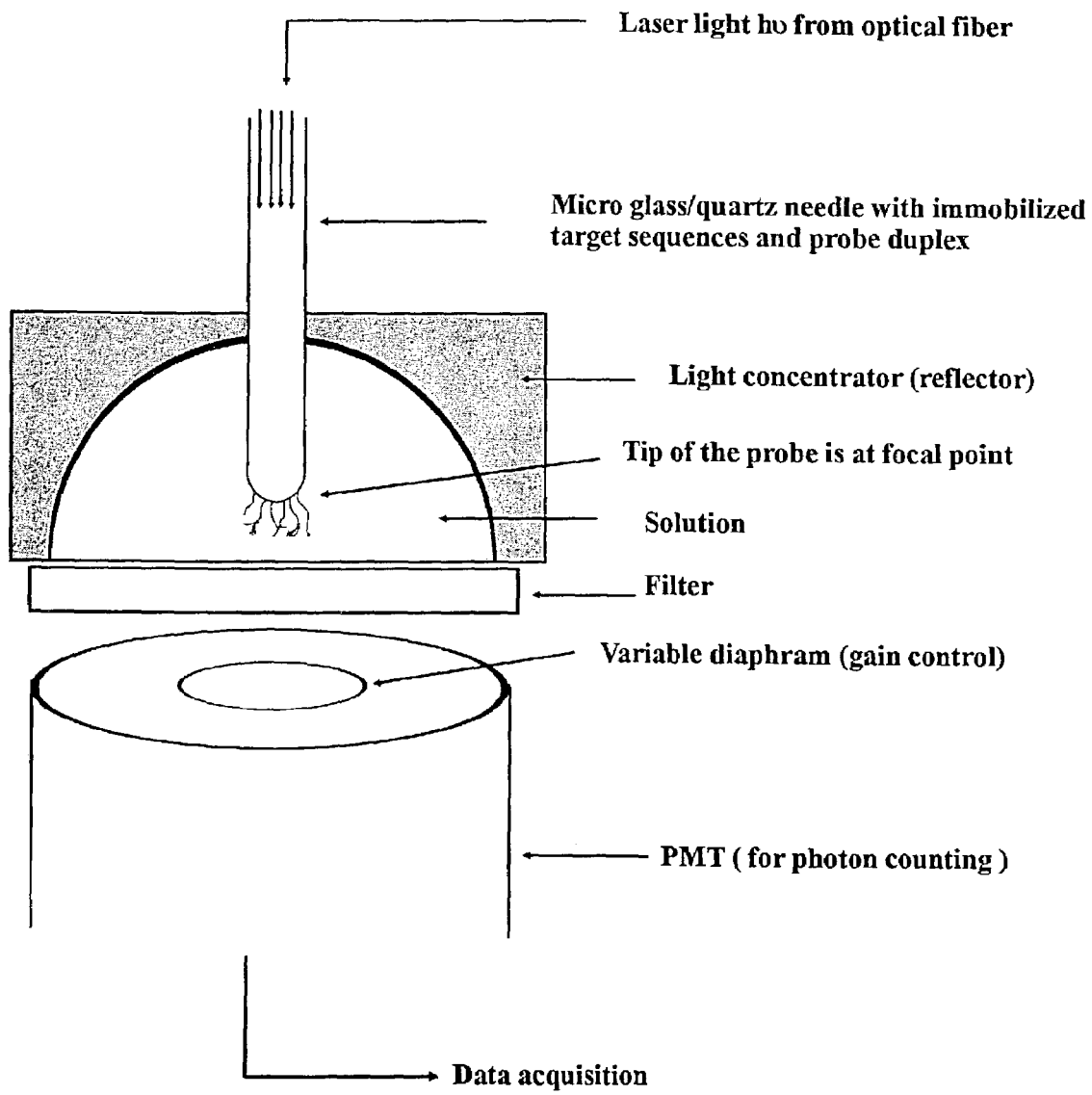
Figure 8B:
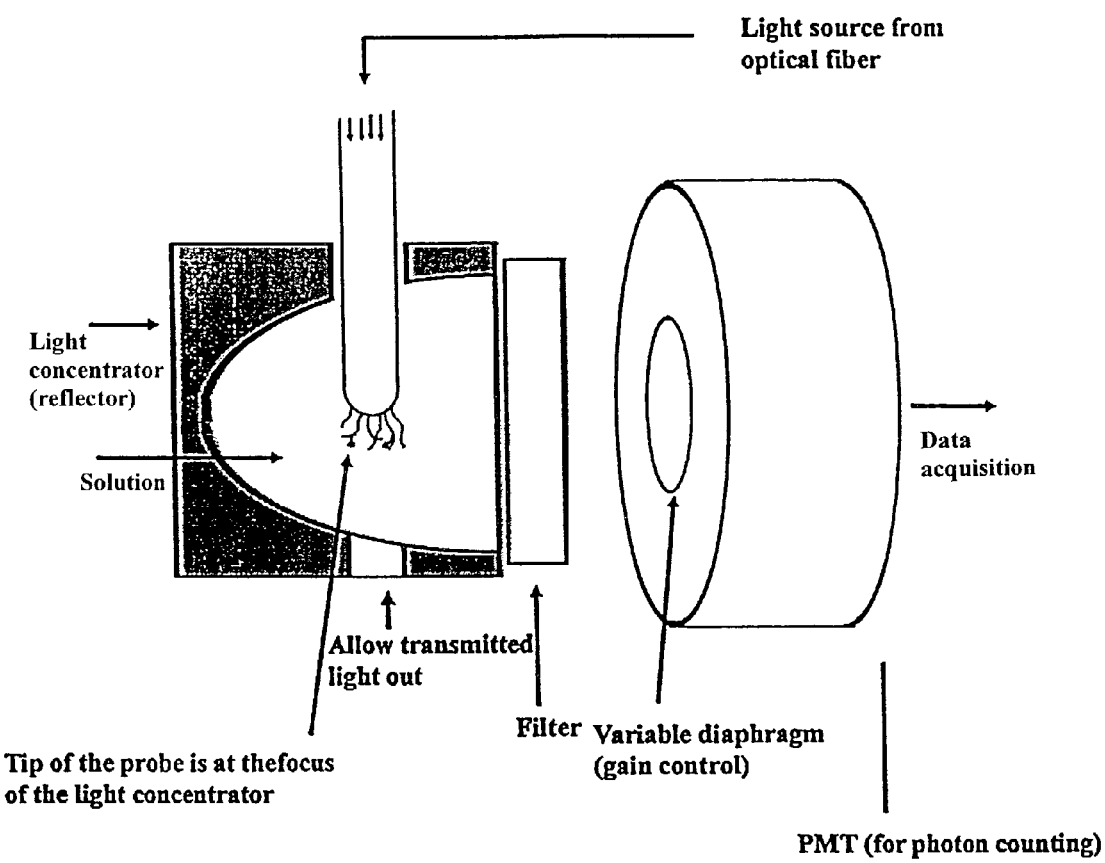
Figure 8C:
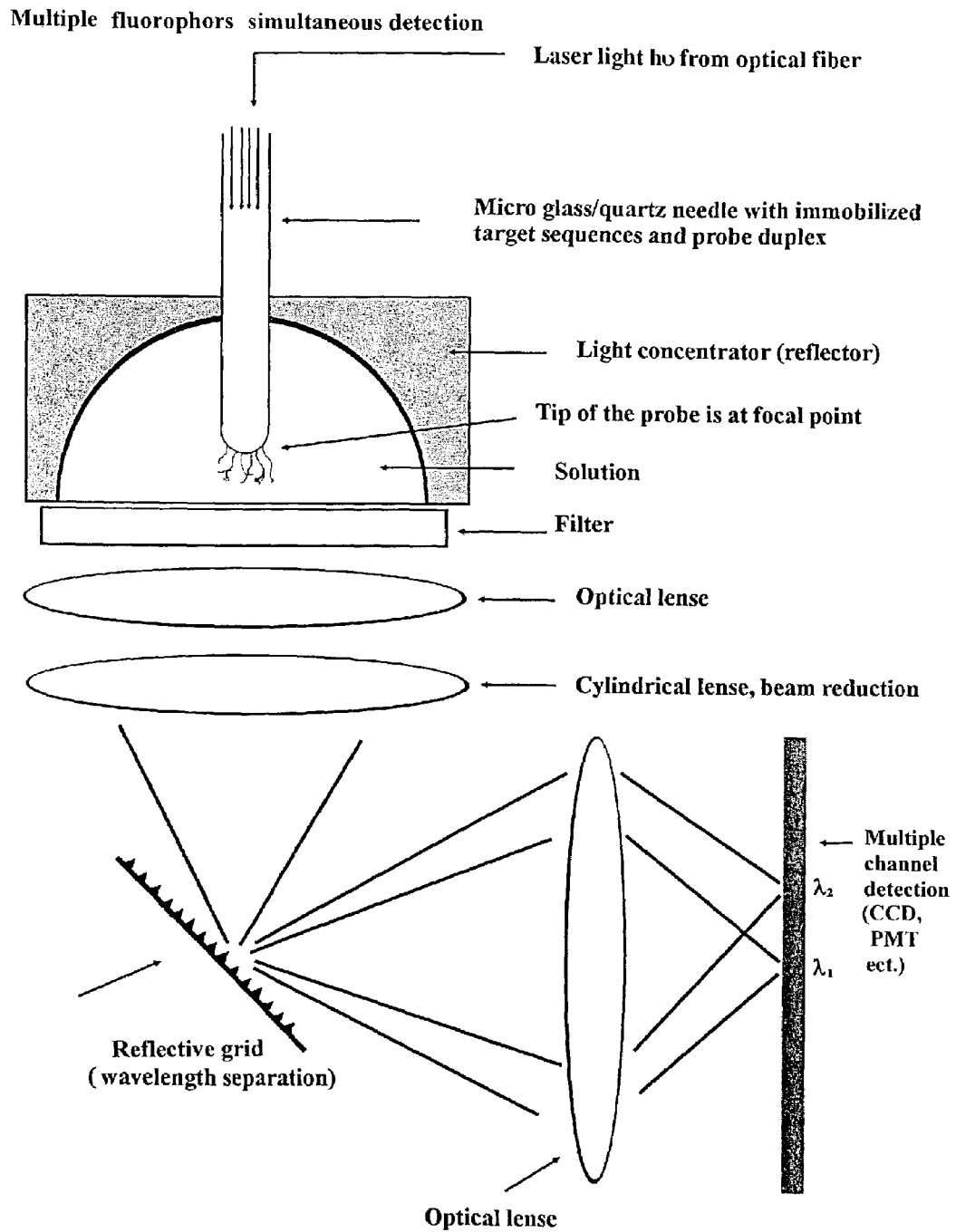

FIGS. 8A, 8B, and 8C further illustrates the optical detection system. It is noted that for the single wavelength analysis (A) and (B), the detection efficiency is up to 90%, and an imaging system is not required.

Figure 9:
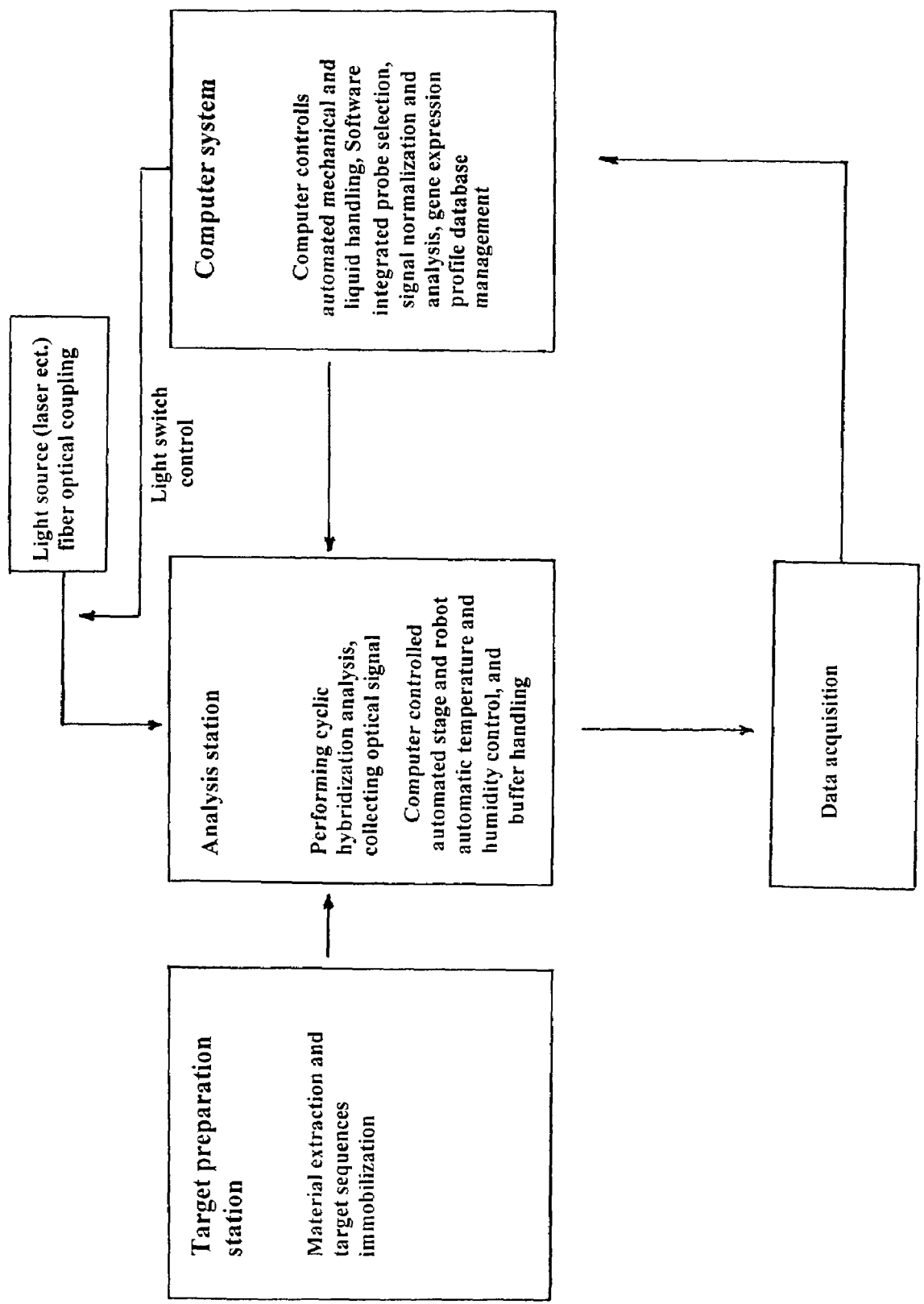

FIG. 9 illustrates a complete system for this analysis method.

Figure 10:
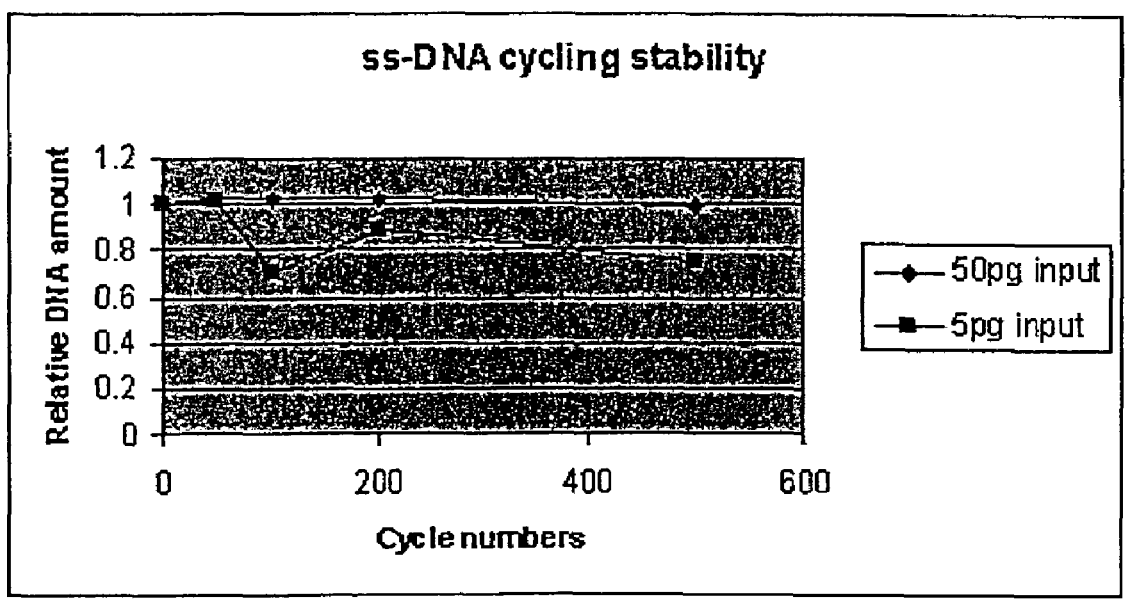

FIG. 10 shows a single-stranded DNA stability test.

DETAILED DESCRIPTION OF THE INVENTION

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "sequentially hybridizing said isolated mRNA or cDNA target sequences with a plurality of nucleotide probes" means that the isolated mRNA or cDNA target sequences are hybridized with a plurality of nucleotide probes sequentially. After hybridizing with one probe, the hybridization between said isolated mRNA or cDNA and the probe is assessed. Then, the probe is dehybridized from the target sequences before the next round of hybridization with another probe. Alternatively, if the existence of the already hybridized probe will not preclude hybridization of the next round of hybridization with another probe, e.g., the two probes will bind with the target sequences at distinct location, the dehybridization of the first probe may not be necessary, provided that the two hybridization events are distinguishable from each other. For example, a detectable signal indicative of the first hybridization event can be quenched or otherwise removed before the second hybridization event. In another example, two non-interfering and distinguishable detectable signals can be used in the two hybridization events.

As used herein, "assessing the sequential hybridization between said isolated mRNA or cDNA target sequences and said plurality of nucleotide probes" is intended to include quantitative and qualitative determination of the identity, amount, homogeneity and any associated chemical, physical and biological properties in connection with the hybridization between the isolated mRNA or cDNA target sequences and the plurality of nucleotide probes, and also of obtaining an index, ratio, percentage, visual or other value indicative of the hybridization. For example, the assessment may be used to determine the presence, absence of amount of the isolated mRNA or cDNA target sequences. Assessment may be direct or indirect. Assessment may also be in any suitable format, e.g., direct, sandwich or competitive format. Depending on the probes and detectable signals generated in the sequential hybridization, each hybridization may be assessed individually or some or all hybridization may be assessed collectively.

As used herein, "abundant class of mRNA or cDNA sequences" means that the target sequences have a cellular expression level of more than 10,000 copies per cell.

As used herein, "intermediate abundant of mRNA or cDNA sequences" means that the target sequences have a cellular expression level of about 300 to about 10,000 copies per cell, e.g., about 300 to 500 copies per cell.

As used herein, "low abundant of mRNA or cDNA sequences" means that the target sequences have a cellular expression level less than 30 copies per cell, e.g., about 10 to 15 copies per cell.

As used herein, "linearly amplifying the mRNA or cDNA target sequences" means that the total copy number of the mRNA or cDNA target sequences is increased while the relative ratio of each mRNA or cDNA target sequence in a mixture is retained.

As used herein, "the nucleotide probes are uniformly labeled" means that the individual probes are labeled to generate same amount of signal regardless the sequences and/or length of each individual probes.

As used herein, "normalization probe" refers to a complimentary sequence to a known nucleic acid sequence other than a target sequence. A known amount or copies of this known sequence is added into the target sample to be immobilized with the target sequences together. The normalization probe is used to calibrate the signal intensity generated from known amount or copies of the known nucleic acid sequence. The information obtained from this calibration can further be used to compare relative abundance of different individual target sequences.

As used herein, "saturation hybridization" means that at least 90% of the target sequences are hybridized with a probe. Preferably, 95%–100% of the target sequences are hybridized with the probe.

As used herein, "complementary or matched" means that two nucleic acid sequences have at least 50% sequence identity. Preferably, the two nucleic acid sequences have at least 60%, 70,%, 80%, 90%, 95%, 96%, 97%, 98%, 99% or 100% of sequence identity. "Complementary or matched" also means that two nucleic acid sequences can hybridize under low, middle and/or high stringency condition(s).

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

As used herein, "two perfectly matched nucleotide sequences" refers to a nucleic acid duplex wherein the two nucleotide strands match according to the Watson-Crick basepair principle, i.e., A-T and C-G pairs in DNA:DNA duplex and A-U and C-G pairs in DNA:RNA or RNA:RNA duplex, and there is no deletion or addition in each of the two strands.

As used herein: "stringency of hybridization" in determining percentage mismatch is as follows:

1) high stringency: 0.1×SSPE, 0.1% SDS, 65° C.;
2) medium stringency: 0.2×SSPE, 0.1% SDS, 50° C. (also referred to as moderate stringency); and
3) low stringency: 1.0×SSPE, 0.1% SDS, 50° C.

It is understood that equivalent stringencies may be achieved using alternative buffers, salts and temperatures (See generally, Ausubel (Ed.) *Current Protocols in Molecular Biology, 2.9A. Southern Blotting, 2.9B. Dot and Slot Blotting of DNA and 2.10. Hybridization Analysis of DNA Blots,* John Wiley & Sons, Inc. (2000)).

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein, "bacteria" refers to small prokaryotic organisms (linear dimensions of around 1 μm) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are 3 main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to obligate intracellular parasites of living but non-cellular nature, consisting of DNA or RNA and a protein. A viral particle referred to in the inventive methods may be a completely assembled virus with any tropism to hosts ranging from prokaryotes to eukaryotes. One of ordinary skill in the art will appreciate that an engineered virus, a partially assembled virus, and genetic and non-genetic component(s) of a virus, a mixture thereof may be an applicable substrate for the transfer. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungi" refers to a division of eucaryotic organisms that grow in irregular masses, without roots, stems, or leaves, and are devoid of chlorophyll or other pigments capable of photosynthesis. Each organism (thallus) is unicellular to filamentous, and possess branched somatic structures (hyphae) surrounded by cell walls containing glucan or chitin or both, and containing true nuclei.

As used herein, "disease or disorder" refers to a pathological condition in an organism resulting from, e.g., infection or genetic defect, and characterized by identifiable symptoms.

As used herein, "neoplasm (neoplasia)" refers to abnormal new growth, and thus means the same as tumor, which may be benign or malignant. Unlike hyperplasia, neoplastic proliferation persists even in the absence of the original stimulus.

As used herein, "cancer" refers to a general term for diseases caused by any type of malignant tumor.

As used herein, "an immune system disease or disorder" refers to a pathological condition caused by a defect in the immune system. The immune system is a complex and highly developed system, yet its mission is simple: to seek and kill invaders. If a person is born with a severely defective immune system, death from infection by a virus, bacterium, fungus or parasite will occur. In severe combined immunodeficiency, lack of an enzyme means that toxic waste builds up inside immune system cells, killing them and thus devastating the immune system. A lack of immune system cells is also the basis for DiGeorge syndrome: improper development of the thymus gland means that T cell production is diminished. Most other immune disorders result from either an excessive immune response or an 'autoimmune attack'. For example, asthma, familial Mediterranean fever and Crohn disease (inflammatory bowel disease) all result from an over-reaction of the immune system, while autoimmune polyglandular syndrome and some facets of diabetes are due to the immune system attacking 'self' cells and molecules. A key part of the immune system's role is to differentiate between invaders and the body's own cells—when it fails to make this distinction, a reaction against 'self' cells and molecules causes autoimmune disease.

As used herein, "a metabolism disease or disorder" refers to a pathological condition caused by errors in metabolic processes. Metabolism is the means by which the body derives energy and synthesizes the other molecules it needs from the fats, carbohydrates and proteins we eat as food, by enzymatic reactions helped by minerals and vitamins. There is a significant level of tolerance of errors in the system: often, a mutation in one enzyme does not mean that the individual will suffer from a disease. A number of different enzymes may compete to modify the same molecule, and there may be more than one way to achieve the same end result for a variety of metabolic intermediates. Disease will only occur if a critical enzyme is disabled, or if a control mechanism for a metabolic pathway is affected.

As used herein, "a muscle and bone disease or disorder" refers to a pathological condition caused by defects in genes important for the formation and function of muscles, and connective tissues. Connective tissue is used herein as a broad term that includes bones, cartilage and tendons. For example, defects in fibrillin—a connective tissue protein that is important in making the tissue strong yet flexible—cause Marfan syndrome, while diastrophic dysplasia is caused by a defect in a sulfate transporter found in cartilage. Two diseases that originate through a defect in the muscle cells themselves are Duchenne muscular dystrophy (DMD) and myotonic dystrophy (DM). DM is another 'dynamic mutation' disease, similar to Huntington disease, that involves the expansion of a nucleotide repeat, this time in a muscle protein kinase gene. DMD involves a defect in the cytoskeletal protein, dystrophin, which is important for maintaining cell structure.

As used herein, "a nervous system disease or disorder" refers to a pathological condition caused by defects in the nervous system including the central nervous system, i.e., brain, and the peripheral nervous system. The brain and nervous system form an intricate network of electrical signals that are responsible for coordinating muscles, the senses, speech, memories, thought and emotion. Several diseases that directly affect the nervous system have a genetic component: some are due to a mutation in a single gene, others are proving to have a more complex mode of inheritance. As our understanding of the pathogenesis of neurodegenerative disorders deepens, common themes begin to emerge: Alzheimer brain plaques and the inclusion bodies found in Parkinson disease contain at least one common component, while Huntington disease, fragile X syndrome and spinocerebellar atrophy are all 'dynamic mutation' diseases in which there is an expansion of a DNA repeat sequence. Apoptosis is emerging as one of the molecular mechanisms invoked in several neurodegenerative diseases, as are other, specific, intracellular signaling events. The biosynthesis of myelin and the regulation of cholesterol traffic also figure in Charcot-Marie-Tooth and Neimann-Pick disease, respectively.

As used herein, "a signal disease or disorder" refers to a pathological condition caused by defects in the signal transduction process. Signal transduction within and between cells mean that they can communicate important information and act upon it. Hormones released from their site of synthesis carry a message to their target site, as in the case of leptin, which is released from adipose tissue (fat cells) and transported via the blood to the brain. Here, the leptin signals that enough has been eaten. Leptin binds to a receptor on the surface of hypothalamus cells, triggering subsequent intracellular signaling networks. Intracellular signaling defects account for several diseases, including cancers, ataxia telangiectasia and Cockayne syndrome. Faulty DNA repair mechanisms are also invoked in pathogenesis, since control of cell division, DNA synthesis and DNA repair all are inextricably linked. The end-result of many cell signals is to alter the expression of genes (transcription) by acting on DNA-binding proteins. Some diseases are the result of a lack of or a mutation in these proteins, which stop them from binding DNA in the normal way. Since signaling networks impinge on so many aspects of normal function, it is not surprising that so many diseases have at least some basis in a signaling defect.

As used herein, "a transporter disease or disorder" refers to a pathological condition caused by defects in a transporter, channel or pump. Transporters, channels or pumps that reside in cell membranes are key to maintaining the right balance of ions in cells, and are vital for transmitting signals from nerves to tissues. The consequences of defects in ion channels and transporters are diverse, depending on where they are located and what their cargo is. For example, in the heart, defects in potassium channels do not allow proper transmission of electrical impulses, resulting in the arrhythmia seen in long QT syndrome. In the lungs, failure of a sodium and chloride transporter found in epithelial cells leads to the congestion of cystic fibrosis, while one of the most common inherited forms of deafness, Pendred syndrome, looks to be associated with a defect in a sulphate transporter.

As used herein, "infection" refers to invasion of the body of a multi-cellular organism with organisms that have the potential to cause disease.

As used herein, "infectious organism" refers to an organism that is capable to cause infection of a multi-cellular organism. Most infectious organisms are microorganisms such as viruses, bacteria and fungi.

B. Methods and Systems for Analyzing Gene Expression Profiles

In one aspect, the present invention is directed to a method for analyzing gene expression profiles of a cell, which method comprises: a) providing for isolated mRNA or cDNA target sequences from a cell; b) sequentially hybridizing said isolated mRNA or cDNA target sequences with a plurality of nucleotide probes; and c) assessing the sequential hybridization between said isolated mRNA or cDNA target sequences and said plurality of nucleotide probes to analyze gene expression profiles of said cell.

Both mRNA and/or cDNA target sequences can be analyzed. For example, the isolated mRNA target sequences from a cell can be provided for and hybridized with a plurality of nucleotide probes. In another example, the isolated cDNA target sequences from a cell can be provided for and hybridized with a plurality of nucleotide probes. In still another example, a combination of the isolated mRNA and cDNA target sequences from a cell can be provided for and hybridized with a plurality of nucleotide probes. Any suitable cDNA target sequences can be analyzed. For example, the first strand cDNA target sequences that are complementary to the mRNA target sequences can be analyzed. In another example, the second strand cDNA target sequences that have the same polarity as the mRNA target sequences can be analyzed. In still another example, a combination of the first and the second strands cDNA target sequences can be analyzed.

The mRNA target sequences can be prepared or extracted from cells using any suitable methods, e.g., any suitable biochemical, cell biological or biophysical methods. See, generally, Ausubel et al., Current Protocols in Molecular Biology, 4. Preparation and Analysis of RNA, John Wiley & Sons, Inc. 2002. For example, the mRNA target sequences can be extracted from cells by a micromanipulator controlled micropipette, adsorption on surface of microwells, extraction with oligo-dT or capillary electrophoresis.

The present methods can further comprise synthesizing first strand cDNA target sequences complementary to the extracted mRNA target sequences. See, generally, Ausubel et al., Current Protocols in Molecular Biology, 5.III, Preparation Insert DNA from RNA, John Wiley & Sons, Inc. 2002. The present methods can further comprise synthesizing second strand cDNA target sequences complementary to the first strand cDNA target sequences. Preferably, the mRNA target sequences and the first strand cDNA target sequences can be degraded or removed from the second strand cDNA target sequences and the second strand cDNA target sequences alone are used in the hybridization with the nucleotide probes. Also preferably, multiple copies of the second strand cDNA target sequences can be synthesized.

The present methods can further comprise removing uninterested mRNA or cDNA sequences from the mRNA or cDNA target sequences prior to the hybridization between the mRNA or cDNA target sequences and the nucleotide probes. The uninterested mRNA or cDNA sequences can be removed from the mRNA or cDNA target sequences by any suitable methods. For, example, the uninterested mRNA or cDNA sequences can be removed from the mRNA or cDNA target sequences using immobilized nucleic acid sequences that are complimentary to the uninterested mRNA or cDNA sequences to remove them from the sample and leaving them behind while the rest of the sample is subsequently transferred away. In another example, the present methods can further comprise removing abundant or intermediate abundant class of mRNA or cDNA sequences from low abundant class of mRNA or cDNA target sequences prior to the hybridization between the low abundant class of mRNA or cDNA target sequences and the nucleotide probes.

In one embodiment, the isolated mRNA or cDNA target sequences can be immobilized to a surface suitable for hybridization analysis prior to the hybridization between the mRNA or cDNA target sequences and the nucleotide probes. Any suitable surface can be used in the present methods. For example, the surface can be a surface of a microneedle or a microsphere. The microneedle can be made of any suitable materials. For example, the microneedle can be fabricated from glass, quartz or plastic. Similarly, any suitable microsphere can be used in the present methods. For example, the microsphere can be magnetic bead or other microfabricated micro-structures with a desired surface property.

In another embodiment, the isolated mRNA or cDNA target sequences can be immobilized to a small area of the surface less than about 10%, 5%, 1% or less of the total surface area and the remaining surface area is treated to prevent nonspecific attachment of the mRNA or cDNA target sequences. For example, the isolated mRNA or cDNA target sequences can be immobilized to the surface of the apex of the microneedle and the remaining surface area is treated to prevent nonspecific association of the isolated mRNA or cDNA target sequences. In another example, the isolated mRNA or cDNA target sequences are immobilized to a surface area ranging from about 1 micron to about 10 millimeters.

The isolated mRNA or cDNA target sequences can be immobilized to the surface via any suitable methods. The isolated mRNA or cDNA target sequences can be immobilized to the surface via covalent and/or non-covalent binding. For example, the isolated mRNA or cDNA target sequences can be immobilized to the surface via an interaction with oligo-dT or oligo-dA that is covalently bound to the surface. The oligo-dT or oligo-dA can be covalently bound to the surface through a flexible spacer or directly. The present methods can further comprise crosslinking the immobilized mRNA or cDNA target sequences to the oligo-dT or oligo-dA. The crosslinking reaction can be activated by any suitable methods or reagents, e.g., photolysis or chemical cleavage.

The present methods can further comprise linearly amplifying the mRNA or cDNA target sequences prior to the hybridization between the mRNA or cDNA target sequences and the nucleotide probes. The mRNA or cDNA target sequences can be linearly amplified by any suitable methods. For example, the cDNA target sequences can be linearly amplified via transcription using the cDNA target sequences as the template. See e.g., U.S. Pat. Nos. 5,514,545, 5,932, 451 and 6,132,997. In another example, the first strand cDNA target sequences can be linearly amplified via synthesizing multiple copies of second strand cDNA target sequences using the first strand cDNA target sequences as the template. Preferably, the mRNA or cDNA target sequences are linearly amplified from about 10 to about 100 fold. Also preferably, the present methods further comprises immobilizing the linearly amplified mRNA or cDNA target sequences to a surface suitable for hybridization analysis prior to the hybridization between the amplified mRNA or cDNA target sequences and the nucleotide probes. This mold of linear amplification is to be distinguished from PCR. The linear amplification employed here is a multiple rounds of duplication of the target sequences by successive rounds of synthesis and subsequent removal of the second strand cDNA. Since it is a faithful duplication, the relative ratio of all species is retained.

The probes can be designed according to any suitable methods. For example, computerized search program can be used to design probe specific to each target sequence with minimal cross hybridization and similar hybridization efficiency. Such exemplary programs include Oligo 5.0 (National Biosciences Inc.), Primer 3 (MIT), and Array Designer (Telechem International Inc.).

The nucleotide probes used in the present methods can have any suitable length, e.g., from about 15 to about 100 nucleotides.

The nucleotide probes used in the present methods can comprise a detectable label. Any suitable label can used. For example, the detectable label can be detected by optical, magnetic, mechanic, spectroscopic, photochemical, biochemical, immunochemical, radioactive or enzymatic means. Preferably, the detectable label is a fluorescent or magnetic moiety. Also preferably, the nucleotide probes are uniformly labeled. Still preferably, the present method is sensitive enough to detect the presence of a single probe.

Depending on the assay purposes, the nucleotide probes used in the present methods can be specific or degenerate probes. Preferably, the nucleotide probes have similar hybridization or dehybridization efficiency.

The nucleotide probes used in the present methods can comprise a normalization probe. Same or different normalization probes can be used in different cycles of the sequential hybridization reactions. The present methods can further comprise assessing expression of an abundant gene as an expression level normalization control.

Since sequential hybridization reactions are used in the present methods, it is desirable that the hybridization speed and efficiency are enhanced. In one embodiment, in at least one of the sequential hybridization reactions, the nucleotide probes are in excess relative to the amount of the mRNA or cDNA target sequences so that the hybridization reaction is a first order reaction or a saturation hybridization. Preferably, in some or all the sequential hybridization reactions, the nucleotide probes are in excess relative to the amount of the mRNA or cDNA target sequences so that the hybridization reaction is a first order reaction and a saturation hybridization. In another embodiment, the molar ratio of the nucleotide probes over the mRNA or cDNA target sequences is about at least 1,000:1.

The hybridization buffer is designed to protect the target sequence from degradation, to promote uniform hybridization and dehybridization and minimize contamination, and also allows the signal to be acquired without loss. In one embodiment, the hybridization buffer comprises an agent to lower the hybridization temperature, e.g., formamide, urea, trimethylammonium chloride, triethylammonium chloride, ethylene glycol and sodium perchlorate, an agent to reduce degradation of the mRNA or cDNA target sequences, e.g., oxygen scavenger, high concentration of monovalent salt, and/or an agent to retain the pH at range from about 6.5 to about 7.5.

The dehybridization between the sequential hybridization reactions, if desirable or necessary, can be effected via any suitable methods, e.g., elevated temperature or changed solution conditions.

If desirable or necessary, the present methods can further comprise removing residual detectable signal from a proceeding hybridization reaction before the next hybridization reaction. In one example, residual fluorescent signal from a proceeding hybridization reaction can be removed by photo bleaching before the next hybridization reaction.

The sequential hybridization reactions can be conducted at any suitable temperature. For example, at least one of the sequential hybridization reactions is conducted at a temperature ranging from about 30° C. to about 60° C. in the presence of a denaturant or a quaternary ammonium salt. Preferably, some or all of the sequential hybridization reactions are conducted at a temperature ranging from about 30° C. to about 60° C. in the presence of a denaturant or a quaternary ammonium salt.

The present methods can be used to analyze expression of any suitable number of mRNA or cDNA target sequences. For example, the present methods can be used to analyze expression of at least 100, 500, 1,000, 5,000, 10,000 or more different isolated mRNA or cDNA target sequences. In another example, the present methods can be used to analyze expression of some or entire population of cellular mRNA or corresponding cDNA from a cell.

The present methods can be used to analyze expression of mRNA or cDNA target sequences isolated from any suitable number of cells. For example, the present methods can be used to analyze mRNA or cDNA target sequences isolated from less than 1,000, 900, 800, 700, 600, 500, 400, 300, 200, 100, 50, 40, 30, 20, 10, 5, 4, 3, or 2 cells. Preferably, the present methods can be used to analyze mRNA or cDNA target sequences isolated from a single cell.

Since sequential hybridization reactions are used in the present methods, same isolated mRNA or cDNA target sequences can be sequentially hybridized to any suitable number of nucleotide probes. The number of the sequential hybridization reactions is only limited by the degradation of the mRNA or cDNA target sequences caused by the hybridization reactions. In one embodiment, same isolated mRNA or cDNA target sequences can be sequentially hybridized to at least 10, 50, 100, 500, 1,000, 5,000, 10,000 or nucleotide probes. Preferably, same isolated mRNA or cDNA target sequences are sequentially hybridized to about 1,500 nucleotide probes within 24 hours.

The speed of the present methods can be enhanced in a number of ways. For example, the isolated mRNA or cDNA target sequences can be hybridized to multiple probes with different labels for detecting multiple target sequences in one hybridization. Alternatively, the mRNA or cDNA target sequences can be subjected to parallel sequential hybridization reactions, i.e., the mRNA or cDNA target sequences are subdivided into multiple groups and each group of the target sequences is analyzed by sequential hybridization with multiple probes. The analysis speed can further be enhanced by combining the above strategies. For example, in at least one of the parallel sequential hybridization reactions, the isolated mRNA or cDNA target sequences in each group can be hybridized to multiple probes with different labels for detecting multiple target sequences in one hybridization. Preferably, in some or all of the parallel sequential hybridization reactions, the isolated mRNA or cDNA target sequences in each group can be hybridized to multiple probes with different labels for detecting multiple target sequences in one hybridization.

Due to the nature of the sequential hybridization reactions, the number of probes need not be predetermined before the sequential hybridization and the number of probes can be adjusted according to the sequential hybridization reaction(s) that has already been performed. In one embodiment, after a number of sequential hybridization reaction(s) is performed, the mRNA or cDNA target sequences can be stored for a time and then re-analyzed with a further hybridization reaction. Similarly, in at least one of the sequential hybridization reactions, the hybridization condition is individually adjusted. If desirable and necessary, in some or all of the sequential hybridization reactions, the hybridization condition is individually adjusted.

The present methods can be used for any suitable purposes. For example, the isolated mRNA or cDNA target sequences can be involved in a biological pathway, encode a group of proteins with identical or similar biological function, expressed in a stage of cell cycle, expressed in a cell type, expressed in a tissue type, expressed in an organ type, expressed in a developmental stage, encode a group of proteins whose expressions and/or activities are altered in a disease or disorder type or stage, or encode a group of proteins whose expressions and/or activities are altered by drug or other treatments. Exemplary diseases or disorders include neoplasm, an immune system disease or disorder, a metabolism disease or disorder, a muscle and bone disease or disorder, a nervous system disease or disorder, a transporter disease or disorder, a signal disease or disorder and an infection.

The present methods can be used to analyze gene expression profiles of any suitable cells. Exemplary cell include an animal cell, a plant cell, a fungus cell, a bacterium cell, a recombinant cell and a cultured cell. In one example, the cell is derived from a tissue or biopsy sample.

In another aspect, the present invention is directed to a system for analyzing gene expression profiles of a cell, which system comprises: a) means for providing isolated mRNA or cDNA target sequences from a cell; b) means for sequentially hybridizing said isolated mRNA or cDNA target sequences with a plurality of nucleotide probes; and c) means for assessing the sequential hybridization between said isolated mRNA or cDNA target sequences and said plurality of nucleotide probes to analyze gene expression profiles of said cell.

The present system can further comprise an instruction for using the means for analyzing gene expression profiles of a cell.

The present system can comprise any suitable means for assessing the sequential hybridization, e.g., an optical device comprising a light concentrator, a filter system and a photomultiplier tube (PMT) unit.

C. Optical Devices for Detecting Hybridization Signal

In another aspect, the present invention is directed to an optical device for detecting hybridization signal, which device comprises: a) a microneedle comprising a mRNA or cDNA target sequence immobilized on its tip and in optical connection with a light source; b) a light concentrator; c) a filter system; and d) a photomultiplier tube (PMT) unit, wherein in operation, hybridization of said mRNA or cDNA target sequence to a complementary probe brings a fluorescent label to the close proximity to said tip of said microneedle, provision of light to said tip from said light source generates fluorescent light from said tip, and said fluorescent light is reflected by said light concentrator to become parallel light passing through said filter system and detected by said PMT unit.

The microneedle can comprise any suitable material. For example, the microneedle can be fabricated from glass, quartz or plastic. The light concentrator can have any suitable shape, e.g., round or oval shape.

The microneedle, the space enclosed by the light concentrator and the filter, and the PMT unit can have any suitable spatial relationships. In one embodiment, the axis of the microneedle and the axis of the PMT unit are parallel. In another embodiment, the axis of the microneedle and the axis of the PMT unit are perpendicular.

The present device can detect a single fluorescent light. Preferably, the present device can be designed to detect multiple fluorescent lights. In one example, the hybridization of the mRNA or cDNA target sequences to a complementary probe brings different fluorescent labels to the close proximity to the tip of the microneedle, and the device further comprises optical means for separating the different fluorescent lights and means for detecting the separated fluorescent lights.

The present device can further comprise other suitable components, e.g., data acquisition and/or processing means.

In an exemplary operation, hybridization reactions can be performed in the matrix wells on a block (see e.g., FIG. 7) that contains individual probes, washing step and dehybridization reactions can be performed in flow channels on the same block. After each washing step following the hybridization reaction, the microneedle can be transferred into the optical detection device for signal detection.

D. Exemplary Embodiments

Exemplary embodiments of the present invention include a system and method thereof that is designed to handle minute amount of initial material and to extract total mRNA transcripts from a single cell or a small cluster of cells. These mRNA transcripts or their cDNA are then immobilized to the surface of a modified glass or quartz needle of small dimensions or small particles, serving as the target for sequential analysis. By hybridizing the target to pre-selected oligonucleotide probes in a sequential manner, the relative as well as the absolute amount of each mRNA contained in the initial material can be quantified. The oligonucleotide probes are uniformly tagged to facilitate their detection/quantitation and are complimentary to different target sequences with minimized cross hybridization. The uniformity in the labeling of the probes allows direct assessment of the number of probes specifically hybridized to the target sequences. By screening through a large number of probes specifically designed to hybridize to different known gene sequences or subsequences, the expression profile of different genes in the sample can be obtained. Typically, expression levels of more than a, few hundred to a few thousand genes can be analyzed from a single sample. Since the detection can be sensitive enough for single probe counting, the expression levels of mRNA species with low copy numbers down to 10–15 per cell can be detected from the initial material of a single cell.

In addition to the ability of handling minute amount of materials from a single cell or a small number of cells, an advantage of these embodiments is the realization that the limited target material (mRNA or their cDNA) can be directly used for repeatedly hybridizing with a large number of probes without appreciable degradation and loss due to handling. By this approach, the target sequences available for analysis is not divided into a large number of "spots", as used in parallel detection (DNA chips, for example). Therefore, there is no need for signal (target sequences) amplification, which often is based on polymerase chain reaction. As pointed out earlier, these amplification schemes (e.g., nested PCR, RT-PCR) contain intrinsic uncertainties that may not retain a linear relationship with the abundance of the initial sequences, especially for those with only a few copies which is the primary application of this invention. Omitting the laborious amplification step also reduces the time needed in preparing the pool of target sequences. This approach is possible because we have found that with our analysis method, the target sequences can sustain repeated temperature cycling (as sometimes required for hybridization analysis of each probe) without appreciable degradation. With a specially designed hybridization buffer, the integrity of the target sequences can be protected during the period of analysis. We further found that under the hybridization conditions used in this method, when the probe is in large excess, the hybridization reaction becomes a first order process, and nearly complete saturation can be achieved in less than ten seconds at a probe concentration of only 10 µM. Therefore, each hybridization cycle, required for the analysis of one gene product can be completed in less than a minute. This is a second advantageous feature of this embodiment, and it provides the basis for sequentially analyzing large number of genes in a reasonable time period (for example, 24 hours) for one analytical cycle. Thirdly, because for low copy number mRNA, only 10–20 transcripts are available in a single cell for analysis. To be able to accurately analyze the expression level of the low copy number mRNA families, a very sensitive device for measuring the hybridization signal from a limited number of copies is designed for this purpose. In terms of applications, this is also a very important consideration because, in a typical eukaryotic cell, there are more than 10,000 species of mRNA expressed only at 10–20 copies. In fact, there are few options available for the analysis of low expression level genes and their physiological significance remain a major difficulty in biomedical research. A fourth embodiment of this invention is to design probes that have similar optimal hybridization/dehybridization efficiency and are also uniformly labeled. Therefore, the detected signal from these labels is linearly related to the total amount of the targets in the analyte. Because of the limited number of labels that can be made available in each probe, the detection method must also be optimized for yielding maximum signal to noise ratio. A further extension of this method that can significantly expand the capacity of this approach (in terms of the number of genes that can be analyzed in a given period of time) is to design probes that have distinguishable labels. As such, in one quantitation cycle, multiple genes can be detected simultaneously. With proper calibration, the relative ratio of these products can be quantitated. Last, since the target materials can be covalently linked to small probe or particles, such as micro needle or magnetic particles, they can be easily handled by simple mechanical devices, therefore, this approach can be fully automated with robotic stations that include the complete analysis of the sample within the chosen gene group. Multiple stations can also be linked together to cover different gene groups, if very large-scale analysis is required.

Figure 1:
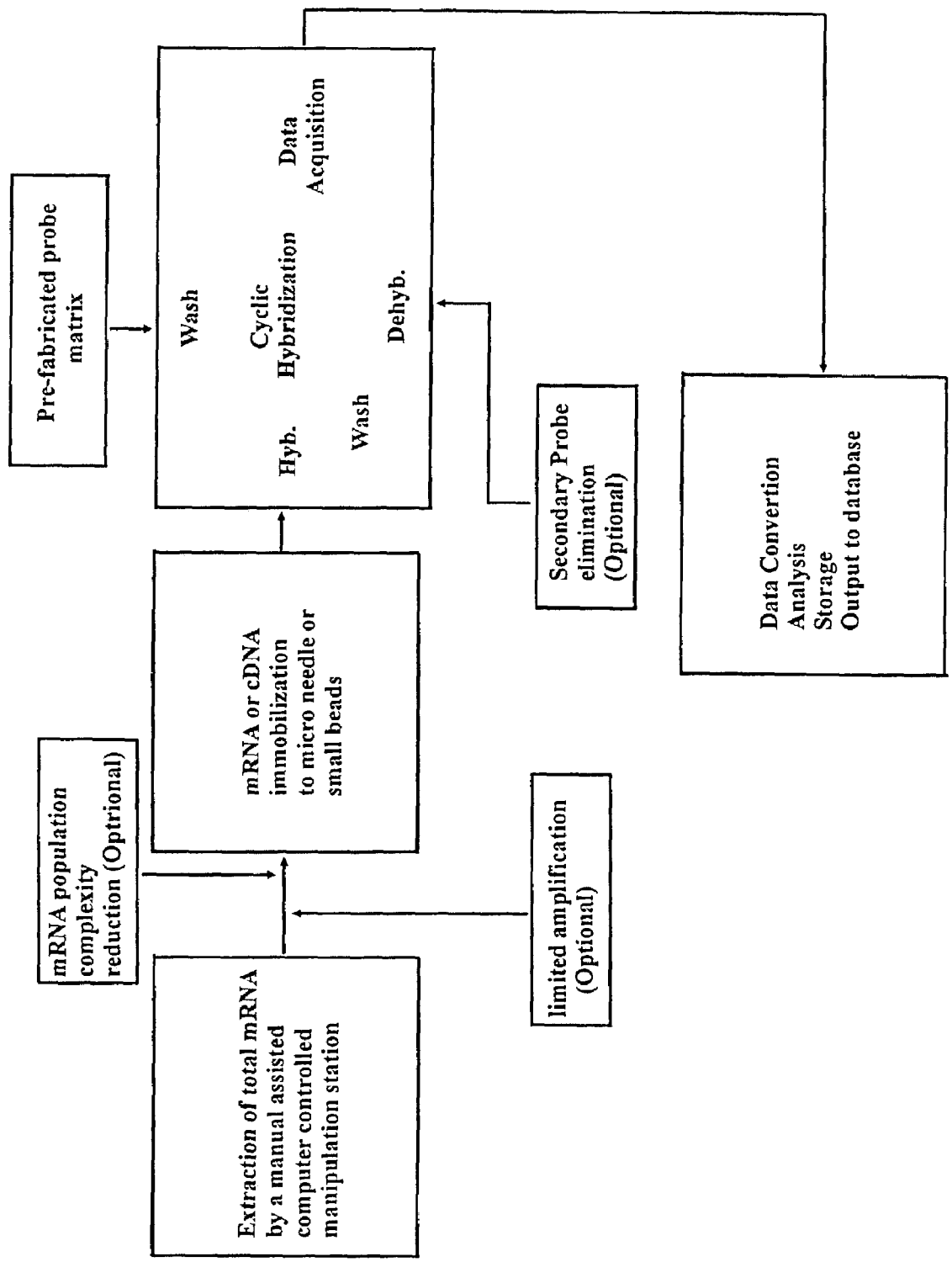

One scheme of these embodiments is illustrated in FIG. 1.

(1) Extraction of Total mRNA from a Single Cell or Small Cluster of Cells and Preparation of the Nucleic Acid Target Sequences a. Extraction Of mRNA Transcripts From a Single Cell or a Small Number of Cells 1. Extraction And Isolation Of Total mRNA Or Their cDNA It is desirable to extract as much material as possible from the very small sample (a single cell, for example). To protect the target sequences from being degraded during handling and analysis, mRNAs can be converted to cDNA using reverse transcription. Several methods are described below for this purpose.

Extraction With Micromanipulator Controlled Micropipettes

In dealing with small cluster of cells or a single cell, a micropipette, which can be prepared to have an outer diameter of 1–10 µm, prepared with a laser pulling machine or a filament heated puller, is used to handle extremely small volume of materials under visual control of an optical microscope. With a micromanipulator/microinjection apparatus, cell or cells from isolated sources (e.g., cells sorted by flow cytometry) or dissected from tissue samples (e.g., laser capture microdissection) are aspirated into the micropipette, and then the content in the micropipette is transferred into a micro well with cell lysis buffer containing desired concentration of denaturant such as GuSCN, Sodium lauryl Sulfate etc. To better protect mRNA from degradation, a cocktail of RNAase inhibitors can be included in the lysis buffer. The cell or cells are lysed in the well and mRNAs are released into the solution (FIG. 2B). Alternatively, a beveled micropipette treated non-adhesive can be directly inserted into individual cell in a biological sample (e.g., whole embryo;

tumor tissue from microdissection) by penetrating its cytoplasmic membrane (FIG. 2A). A negative pressure in the pipette can extract a large fraction of the cytoplasm which can be transferred into a micro well for mRNA capture and then into a buffer solution of choice (for example, reverse transcription buffer, special hybridization buffer, or others). The micro well is coated with covalently linked oligo-dT sequences to capture mRNA transcripts. In a specially formulated cell lysis buffer, mRNA can hybridize with oligo-dT sequences and are captured in the well. The cell lysate can be removed and the mRNA can be resuspended in a different buffer. By changing buffer and/or elevating temperature, mRNA can be dissociated from the oligo-dT sequences and transferred into a new well. The mRNA in the new well can then be used for immobilization. The extraction procedures are carried out in a concealed chamber under humidity control (to prevent solution loss due to evaporation). This micro well capturing step allows quick separating of the mRNA population from other cellular constituents and exchanging buffer solution of choice.

mRNA Conversion Into cDNA

Although the eluted mRNA in buffer solution can be used for immobilization, they can be reverse transcribed into cDNA for better stability and easier handling. Right after they are transferred into the micro well with appropriate buffer, reverse transcriptase (e.g., MMLV, Retrotherm, rTth) and oligonucleotides are added to transcribe mRNA into first strand cDNA sequences, using oligo-dT as primers. Once all mRNA strands are converted into poly-dT cDNA strands, RNase H is added to remove the original mRNA strands, and cDNA strands are left in the solution in the micro well. This conversion step after isolation allows minimum handling of mRNA, which will protect the integrity of the target nucleic acid sequences especially for those rare species of only 10–20 copies per cell.

Second Strand cDNA Synthesis

In a more preferred approach, second strand cDNA is synthesized and used for target immobilization. In this particular method for mRNA capture, first strand cDNA can be synthesized in the micro well once mRNA formed duplex with the immobilized oligo-dT sequence on the walls of the micro well, using reverse transcriptase. Then, second strand cDNA sequences can be synthesized with RNase and DNA polymerase. Since the first strand cDNA sequences are covalently linked to the micro well through their oligo-dT end, the second strand cDNA sequences can be eluted from the duplex by denaturation in a special buffer or at an elevated temperature. The collected second strand cDNA, which represent the exact abundance of all mRNA species present, are used in target immobilization. The use of the second strand cDNA sequences simplifies later immobilization procedure. The use of only single stranded cDNA instead of double stranded cDNA as target improves probe hybridization efficiency in analysis. Multiple rounds of second strand synthesis can also be performed to improve signal to noise ratio or to facilitate parallel analysis (see below).

Isolation of Total mRNA or cDNA by Capillary Electrophoresis

To separate mRNA or the cDNA derived from mRNA from other constituents in the cell, cell lysate can also be loaded onto a capillary electrophoresis device, running through capillary can separate total mRNA from other cellular contents. When the fraction contains the mRNA/cDNA population is identified after the sample has gone through the capillary, it can be collected again with a micropipette and transferred into a micro well. The isolated clean mRNA or cDNA fraction can increase the efficiency of immobilization.

In any of these procedures, the final volume of the solution containing mRNA or cDNA can be easily controlled with evaporation or addition of extra volume of desired solution. This is important when the target sequences are physically linked to small probes or particles (see below).

2. Complexity Reduction and mRNA Species or their cDNA Selection for Analysis

Even though the total mRNA or their cDNA can be used as targets for analysis, the solution can be treated to reduce complexity of the targets. In a typical mammalian cell, there are three different groups of mRNA populations: the abundant class, the intermediate (or intermediate abundant) class, and the scarce (or the low abundant) class. Abundant class has more than 10,000 copies per cell and usually consists of "housekeeping" genes. These genes are well characterized by the array technology and other methods. The intermediate class can have 300–500 copies per cell and consists of about 500 different species. The scarce class is only expressed at much lower level, e.g., 10 to 15 copies per cell, but consists of most of the species (>10,000) in RNA messages. In many cases, the interests of analysis are a set of genes that belong to a specific pathway, or mRNA transcripts belong to the intermediate and scarce classes. To reduce the complexity introduced by the existence of the abundant class, several approaches can be used to remove the abundant class mRNA species and uninterested species. In one approach, a micro probe such as a micro glass needle or micro beads, which are covalently linked with sequences complimentary to those unwanted mRNA or cDNA species, is hybridized to the mRNA or cDNA solution in the micro well. After hybridization, the selected mRNA or cDNA species formed double stranded hybrid with the sequences covalently linked on the micro probe. Then the micro probe is removed together with those mRNA or cDNA of selected species, and the mRNA or cDNA solution is left with the population of interest. In another approach, the micro well can be covalently linked with sequences complimentary to those unwanted mRNA or cDNA species. Once the mRNA or cDNA solution is hybridized with the coated sequences in the micro well, the reduced mRNA or cDNA solution can be obtained by simply withdrawing the solution and transferred into a new micro well. Those selected species are retained in the preceding well.

b. Crosslinking of Target Nucleic Acid Sequences to Small Probe or Particles

1. Picking Up mRNA or cDNA Derived from mRNA from the Extracted Solution

To pick up Poly-A tailed mRNA and second strand cDNA or first strand cDNA, a micro probe covalently linked with oligo-dT or oligo-dA oligonucleotides is used. The micro probe can be any desired material such as a glass (or quartz) micro-needle (a cantilever-attached glass tip in case mechanic detection is used) or magnetic beads. To make this kind of micro probe, oligo-dT/oligo-dA oligonucleotide sequences can be covalently linked to glass or quartz surface through several different chemical reactions. In one example, the glass surface can be derivatized to contain carboxyl group —COOH. 5'-amine terminated oligo-dT can be synthesized by standard phosphoramidite chemistry. Oligo-dT is then covalently linked to the micro-needle by activating the carboxyl group on the glass or quartz surface using carbodiimide (e.g. EDAC, EDC, CMC). The length of oligo-dT can vary from 10–40 for optimal hybridization efficiency to Poly-A mRNA. To ensure that all nucleotide sequences bind to localized area, only a small area on the glass or quartz surface is derivatized (FIG. 4) and linked with oligo-dT, and the remaining area on the micro probe is treated (siliconized) to prevent non specific adsorption. Using such an oligo-dT/oligo-dA coated micro probe, there are only small variations in protocols for picking up different target sequences (as below).

mRNA Or Second Strand cDNA in Solution mRNA or Second strand cDNA is suspended in hybridization solution in a micro well. After hybridization of mRNA or second strand cDNA to oligo-dT on the glass or quartz surface completes, micro-needle bound with all mRNA or cDNA material is transferred to a new well where further process will take place.

First Strand cDNA in Solution

For better stability and easier handling, mRNA is converted into first strand cDNA right after they were captured and transferred in the micro well in the extraction process. To pick up the first strand cDNA for direct use in hybridization analysis, the micro probe, which is covalently linked with oligo-dA oligonucleotides, is used.

To efficiently pick up initial material, a specially formulated buffer can be added into the micro well to increase effective nucleic acids concentration, and therefore accelerating the hybridization process. The time required for 90% picking up can be calculated as in the following example: an area of 50 μm square on the micro glass/quartz needle is covalently linked with oligo-dT sequences in a density of one site per 25 nm2, therefore the total number of oligo-dT sequences is $1 \times 10^8$. When the hybridization is carried out in a micro well of 100 nanolitters in volume, the time required to reach (1−x)% hybridization is defined by the equation:

$$t_x = \ln(1/x)/(k_0 * C * n^{0.5})$$

wherein x is the fraction of original material remained unhybridized; $k_0$ is the rate constant of the reaction; C is the effective concentration of oligo-dT sequences (in this case is $1 \times 10^8 / 100$ nl); n is the length of oligo-dT sequence (usually 25)); the rate constant $k_0$ is $1.7 \times 10^5$ as derived from the experimental results as presented in FIG. 6).

The time for $t_{90\%}$ is less than 30 minutes in the above estimate. With the specially formulated buffer included, the reaction can be accelerated even further, which reduces the time for preparing target sequences to minimum as compared to the laborious and time-consuming amplification and labeling procedure involved in current array technology.

2. Immobilizing Target Nucleic Acid Sequences for Analysis

Once mRNA, first or second strand cDNA hybridized to oligonucleotide sequences on the micro probe, they can be immobilized on the probe by crosslinking or conversion to the covalently linked cDNA strand for the use as target nucleic acid sequences in sequential hybridization analysis.

First Strand cDNA Hybridized to Oligo-dA

In the case that mRNA transcripts are converted into first strand cDNA sequences in the micro well and then picked up with the oligo-dA sequences on the micro needle, immobilization of the cDNA as target sequences can be realized by crosslinking cDNA to oligo-dA oligonucleotides. When a crosslinking agent is incorporated in oligo-dA synthesis, by activating the cross-linker after hybridization, oligo-dT strand and its bound cDNA are covalently linked, and therefore immobilizing first strand cDNA to the solid surface. In one example, synthetic oligo-dA is modified with a base pair cross-linking agent, psoralen. After cDNA hybridized to oligo-dA, ten to twenty minutes of UV irradiation at 350 nm can be used to cross-link cDNA to oligo-dA.

mRNA Hybridized to Oligo-dT mRNA transcripts can be directly used in hybridization analysis if desired. In the case where mRNA transcripts are directly used as the target sequences, after mRNA hybridized to the oligo-dT sequences covalently linked on the glass or quartz micro needle, immobilization can be achieved through a crosslinking agent (e.g., psoralen) that is contained in the modified oligo-dT sequence. However, since RNA is easily degraded even under most stringent controls in a prolonged procedure, it is preferred to use cDNA sequences for analysis, as they are more stable than mRNA and easier to handle. For this purpose, reverse transcriptase is added to transcribe mRNA into cDNA using the paired oligo-dT as the primer. Since oligo-dT primers are already covalently linked to the solid surface, synthesized cDNA are immobilized without further processing. Then mRNA transcripts can be denatured from cDNA or removed by adding RNase. Single stranded cDNA immobilized on the surface of the micro needle are ready to be used as target sequences for hybridization analysis.

Second Strand cDNA Hybridized to Oligo-dT

During the extraction step, second strand cDNA are synthesized for simplified immobilization. After second strand cDNA hybridized to oligo-dT on the micro probe, first strand cDNA can be synthesized with T4 DNA polymerase, using oligo-dT as the primer. Then the second strand cDNA can be denatured from the duplex, leaving a single stranded cDNA covalently linked to the micro probe. The immobilized first strand cDNA can then be used as target sequences for hybridization analysis.

In all the above extraction, isolation, and immobilization procedures, the target sequences used in this method are exact representations of every species in original material. There is no potential problem of non-linear amplification of different species from the original material as seen in those methods wherein PCR is used to amplify the total nucleic acid targets.

Linear Amplification

For extremely low copy messages, a linear amplification, preferably limited linear amplification, of mRNA may be employed. In one example, cDNA can be transcribed in vitro to make many copies of antisense RNA (aRNA) if using a hybrid primer containing both oligo-dT and a RNA polymerase promoter site during reverse transcription. It is shown that this transcription process is not sensitive to the length of the cDNA, therefore, the resulting aRNA should remain linearly related to the number of cDNA copies. This procedure may confer 100–1,000 fold linear amplification of initial material regardless of mRNA species, and the in vitro synthesized aRNA can be converted into cDNA at the end of the amplification, thus increasing the number of cDNA copies available as target sequences for analysis. In situ aRNA amplification technique has been implemented in single cell lysates in some studies, but the effectiveness of the approach has been hindered by the low efficiency in mRNA reverse transcription and contamination from rRNA in the cell. In this mRNA extraction method, the captured mRNA in micro well is more suitable for efficient reverse transcription since the cellular constituents (e.g., rRNA, ribosome) are removed during the capturing step. The amplified population is only mRNA. This in vitro transcription amplification and conversion process can be directly carried out in the micro well, and the 100–1,000 fold linearly amplified cDNA can be used for immobilization. To best preserve the linear relationship of amplified target to the initial material, further amplification of a second round, or some polymerase chain reaction (PCR) based procedures should be avoided and the amplification factor should be kept low, since the error in any amplification scheme should be accumulative.

However, there is a simpler procedure that can be employed with the specific mRNA capturing method used in this invention to amplify the original material to a limited extent. As indicated earlier, once mRNA transcripts are captured by the oligo-dT sequences immobilized on the micro well, cDNA sequences can be synthesized with reverse transcriptase. The immobilized first strand cDNA sequences can be used as a template to synthesize second strand cDNA. The second strand cDNA can then be denatured and eluted from the immobilized first strand cDNA for the use as the target sequences. Since the first strand cDNA sequences are reusable, another round of the second strand cDNA synthesis can generate an exact duplicate of second strand cDNA pool as the first round synthesis. Therefore the original target sequences are amplified twice. With five to ten rounds of second strand cDNA synthesis, the original material is effectively duplicated five to ten times. Although this limited amplification procedure does not provide the same degree of amplification as the antisense RNA amplification method, it is enough to significantly improve signal detection for the sensitive hybridization detection device used in this invention. The key advantage of this procedure is that second strand cDNA synthesized in each round is an exact duplication of original mRNA material. There is no nonlinear amplification involved in this method, therefore provides the great confidence in interpretation of the hybridization results obtained with amplified target sequences. The duplicates of target sequences can be analyzed with different probe matrices in parallel, thus significantly expand the number of genes that can be analyzed with this sequential hybridization analysis method in a certain period of time.

Figure 3:
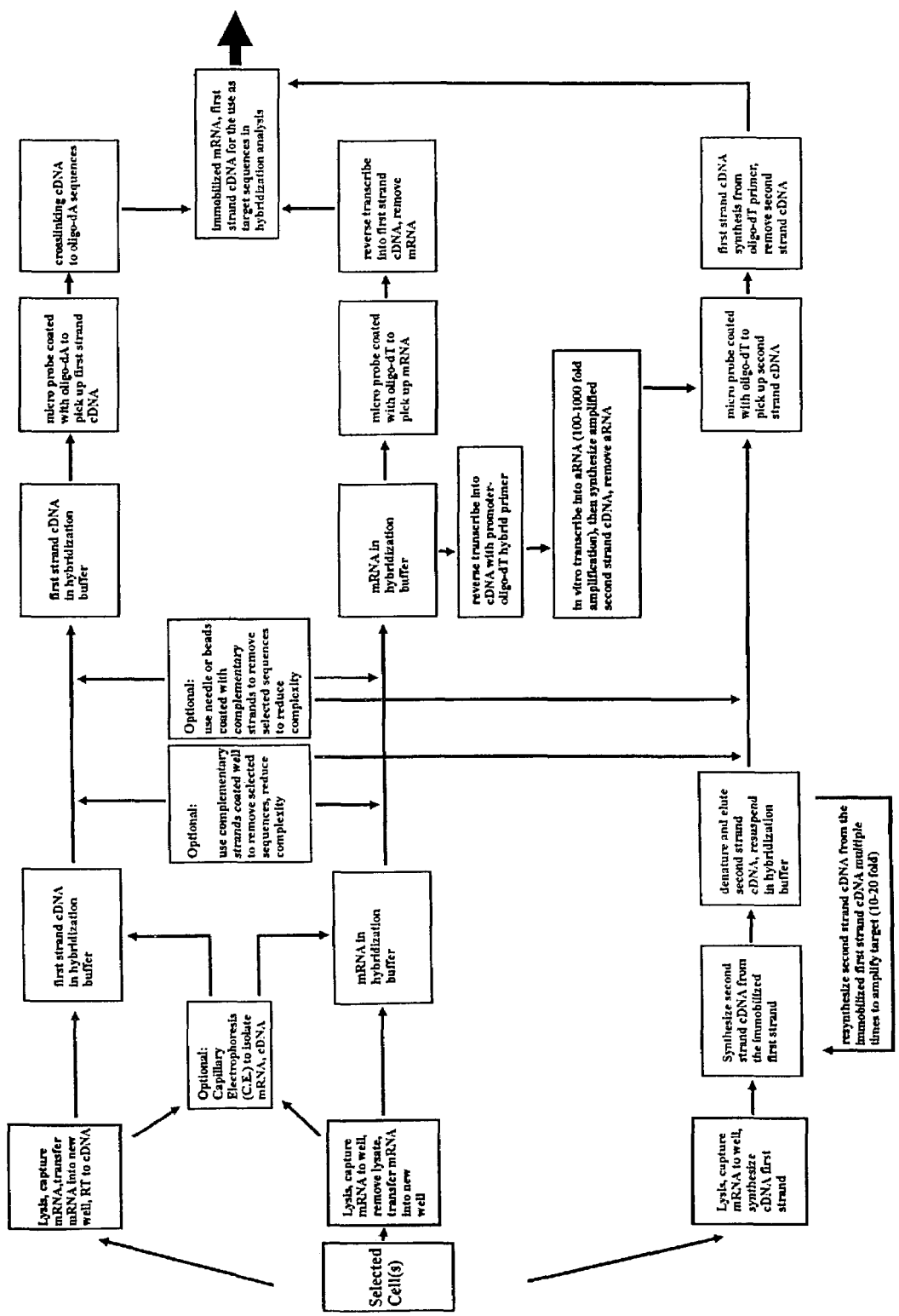
FIG. 3 shows a block diagram, illustrating the procedures in target material extraction, preparation and immobilization.

These procedures are illustrated in FIG. 3.

(2) Hybridization Probe Synthesis, Labeling, Design and Selection a. Hybridization Probe Synthesis and Labeling The sensitivity of this technology depends on the amplification of the hybridization signal and the accuracy of quantitation depends on the uniformity of the probes. Oligonucleotide sequences of 15–100 nucleotide length can be generated by standard solid-phase synthesis technology for use as hybridization probes. Detectable labels on the probes can include any composition detectable by optical, magnetic, mechanic, spectroscopic, photochemical, biochemical, and immunochemical means. There are a number of ways to uniformly label the oligonucleotide sequences for use in hybridization. It is also important to realize that the labels attached to the hybridization sequences should impose a minimum influence on the hybridization efficiency, which is important in increasing the number of cycles that can be applied for each run of analysis (i.e., in a fixed time period).

For Optical Detection:

Fluorescent labeled nucleotide (e.g., fluorescein and rhodamin nucleotides), or biotinylated nucleotide (e.g., biotin-dCTP and biotin-dUTP) can be directly incorporated during synthesis of the hybridization probes. The fluorescent labeled probes can be detected directly by optical methods. The biotin labeled probes can be made detectable by adding a streptavidin conjugated fluorescent label. Fluorescent labels such as fluorescent protein, fluorescent micro beads, nanocrystals, fluorophor containing small particles are suitable for this labeling procedure. It is preferable to have only one reaction site available in the streptavidin conjugated label to ensure uniformity in labeling. The advantage of this biotin coupling procedure is that a much stronger fluorescent label can be coupled to maximize the available signal for detection.

In a more preferred approach, the oligonucleotide sequence is covalently linked to a label after synthesis. To achieve the desired result, a modified nucleotide can be incorporated during the synthesis of the hybridization probe. The modification can be a chemical reactive or photo-reactive site. On the other hand, desired label is synthesized to contain one site that is able to react with the site in nucleotide to form covalent bonds. One unique site in each probe guarantees the single labeling of the hybridization probe.

In one particular example, a double stranded DNA molecule is synthesized with fixed number of fluorescent nucleotides, and this DNA fragment can serve as a fluorescent tag. Hybridization probes can be ligated (e.g., using DNA ligase) or linked to this DNA fragment. Since there is only one reactive site, the probes generated are uniformly labeled. There are different approaches that can be used to synthesize the fluorescent DNA with fixed number of fluorophors. In one particular example, a DNA fragment of random sequences can be designed in such a specific way: it consists of 15 (as an example) random nucleotide sequences, and the sequences can be 15 copies of the same sequence, or multiple copies of different sequences, with each of 15–25 nucleotide in length. The rationale here is to incorporate only one fluorescent nucleotide in each short sequence during synthesis. This can be achieved in several ways: one way is to directly synthesize short nucleotide sequences with only one fluorescent nucleotide in each sequence, then anneal these oligonucleotides to a complimentary single strand DNA of all 15 sequences. By repairing the nick (e.g., using RNA ligase, or DNA ligase) and cross-linking the duplex (e.g., with photoactive or chemical-active site introduced in the end of each sequence), a double stranded DNA fragment with fixed fluorophors is generated. Another way to synthesize the DNA fragment is to design the sequences in such a way that a particular nucleotide (A, or T, or G, or C) only occurs once in any of the short sequences. The DNA fragment can then be synthesized by PCR with that fluorescent nucleotide, and the single strand with 15 fluorescent nucleotides at defined location is obtained by separating from the other strand. This can be achieved easily by immobilizing the other strand on a solid surface and denature the double stranded DNA and then elute the single strand of the desired. The eluted uniformly labeled single strand DNA is then annealed with a single strand fragment of its complementary sequence. The duplex can be cross-linked to generate the double strand DNA with fixed number of fluorophors. The above methods provide means for synthesizing a uniform fluorescent label of multiple fluorophors. The reason to select each short sequence of 15–25 nucleotides with only one fluorophor is that the distance between two closely located fluorescent nucleotides is far enough to eliminate self-quenching, and yet the total length of the labeled double stranded DNA is short enough not to significantly affect hybridization of the probe to the target sequence. Of course, it is advisable to select fluorophores that has a short quenching distance (thus allowing more fluorophores to be included in a given length of double stranded DNA) and appropriate hybridization buffers that may minimize the effect of this dsDNA label on hybridization. It is also contemplated that low salt solution may be used at the data acquisition stage to extend the dsDNA (to minimize self quenching). This labeled double strand DNA fragment is then ligated (e.g., using RNA ligase) or cross-linked (by photo-active or chemical-active cross-linkers) to the hybridization probe. FIG. 5 is a detailed illustration of the procedure for the preparation of uniformly labeled fluorescent DNA fragment synthesis.

For Mechanic or Magnetic Force Detection

Similar as the labeling of probes for optical detection, probes used in this type of detection can incorporate a biotin linker or chemically modified 5' terminal (e.g., 5'-Amine modified). The labeling is accomplished by introducing streptavidin conjugated magnetic beads or magnetic beads with chemically modified surface (e.g., —COOH carboxylated) to the probe. Under specific conditions, the labeling is uniform and can result in one bead per probe.

Uniformity of the labeled probes is preferred for direct quantifying hybridization events, and it provides confidence in single probe counting in signal evaluation. This is very important for measuring genes expressed at low level of 10–15 copies per cell if initial material is from only a single cell or few cells.

B. Hybridization Probe Design and Selection

Probe Design

Hybridization probes used in this embodiment are oligonucleotides that range from 15 to 100 nucleotides in length. The longer ones have the advantage of minimizing the possibility of cross hybridization and increasing the stability of the hybrid duplex, yet without significant impact on the hybridization kinetics. They have sequences complementary to subsequences of mRNA or cDNA of particular genes, depending on whether mRNA messages or cDNA derived from mRNA are used as target sequences. They can be designed to be unique in the genome to avoid cross hybridization, and also lack secondary structures that could interfere with hybridization. In a more sophisticated design, combinatorial probes that hybridize to the same gene can be selected as a group to better discriminate cross hybridization events and non-specific binding, therefore improving the confidence in data interpretation. One consideration in designing hybridization probes is that with 10 molecules to be detected in a population of $10^7$–$10^8$ species in total mRNA or cDNA, the probe should bind to the specific target $10^8$ stronger than other sequences. In energy terms, this means 18 kcal/mol, which translates to about 10–15 mismatches. Therefore hybridization probes can be designed to have at least 10–15 mismatches to the rest of the sequences to assure high specificity. In one example, the oligonucleotides can be designed to be 30–60 nucleotides long to reduce cross-hybridization probability. One mismatch of base pairing affects melting temperature by 1° C. in a 60-nucleotide probe. Ten mismatches would affect melting temperature by 10° C. The difference in melting temperature between perfect matched and imperfectly matched hybrids makes it easy to differentiate specific and no specific hybridization events by optimizing hybridization and washing conditions.

Probe Selection and Optimization

There are virtually unlimited probes that could be used for hybridization analysis. In practice, many of them are not suitable due to low hybridization efficiency, internal secondary structures, and cross hybridization. Selecting best probes for analysis is also an important task for designing an assay monitoring expression levels of many different genes. Once group of probes are designed by special software (see e.g., Oligo 5.0 (National Biosciences Inc.), Primer 3 (MIT), and Array Designer (Telechem International Inc.)) and synthesized for testing, and this method provides a procedure to select probes that bind to their specific complementary sequence with high efficiency and low cross hybridization occurrence. First, mRNA or cDNA of the specific target gene is immobilized on the micro needle at a known amount. Performing hybridization to probes that are designed specifically for this target, we can distinguish the properties of the different probes in their hybridization efficiency. Probes bind to the target sequence most efficiently will be selected. Then a pool of cDNA or RNA made from cDNA library, which lacks the specific target gene, is used to select probes with minimum cross hybridization property. Hybridizing this pool of target nucleic acid sequences to those probes selected for their high efficiency in binding to target genes, the ones with extremely low or no cross hybridization signals can be selected from the group. Therefore a population of probes with high specificity and little or no cross hybridization activity are generated by this reduction procedure. Since hybridization probes are in free suspension in solution, there is no tedious work involved in synthesizing new arrays of selected probe group. Any probe can be readily included in test matrix in this reduction procedure.

Internal Normalization Control

To monitor the efficiency in preparing immobilized target nucleic acid sequences from the sample, a known amount of nucleic acid sequence that has no similarity to target sequences for analysis can be included in the immobilization step to serve as an internal control. Probes that hybridize to this sequence can be included in the analysis. They can be used to calibrate the signal in detection since the number of target sequences is known. As this method involves sequential analysis, normalization probes can also be included at different time points during the analytical cycle to monitor the integrity of the target sample.

Expression Level Normalization Control

The total expression level varies in individual cells depending on the state and metabolic activities. It can also change overtime for the same cell. The changes will reflect in both constitutively expressed genes and target genes for analysis. Although this invention directly measure the number of nucleic acid targets of interested gene transcripts, to better understand the differential expression of the target genes in question, the constitutively expressed genes can be used as an overall expression level standard. Any constitutively expressed "housekeeping genes" can be used according to experimental convenience with the proper scaling of signals in detection.

(3) Sequential Quantitation by Hybridization

A feature and advantage of this embodiment is to quantitate the amount of target sequences linked on micro needle or beads by repeated, sequential hybridization of selected probes to the target in the shortest possible time without compromising either the sensitivity or the reliability of the measurements. For the hybridization procedure, vast excess of the probe is provided to drive the process into a first order reaction, therefore the saturation is achieved rapidly. After quantitation of the amount of hybridized probes, they can be removed by dehybridization in order to start the next cycle, or the labels can be selectively "silenced," which can be achieved when proper labels are used.

a. Hybridization Kinetics

In this embodiment, each hybridization experiment is carried out in micro wells filled with hybridization buffer. Since hybridization probes are in free suspension in solution and can be added in large excess than the target sequences, the hybridization reaction becomes a pseudo-first order reaction at this high probe concentration. The time required for hybrid formation is represented as the following equation:

$$t_x = N * \ln(1/x)/(k_0 * P * n^{0.5})$$

wherein $t_x$ is the time for x fraction of the initial target remaining unhybridized; $k_0$ is the reaction rate constant; P is the nucleotide concentration of the probe (concentration of the probe*number of nucleotides); N is the complexity of the oligonucleotide probe (in this case, it is the nucleotide length of the probe); n is the nucleotide length of the probe.

The reaction rate only depends on the concentration of the probe and is independent of the concentration of the target sequences. FIG. 6 shows an experiment of hybridization kinetics of immobilized oligo-dT sequence to single stranded DNA fragment containing oligo-dA sequence. Based on these measurements, $k_0 = 1.7 \times 10^5$. For a probe of 25 nucleotides in length and a concentration of 20 μM in the hybridization well, the time required for 90% of the target sequences to hybridize with the probe is less than 5 seconds. Therefore, this rapid kinetics allows the completion of the analysis of each gene product in a minute, including the time required to clean the sample, data acquisition for quantitation and dehybridization or label elimination. Accordingly, in 24 hrs, nearly 1,500 genes can be analyzed with single wavelength detection. Any limited parallel detection (via multiple wavelengths, or duplicated target sequences) will significantly improve this capacity.

b. Hybridization Condition and Optimization

Hybridization conditions, such as salt concentration, temperature, denaturing additives, affect hybridization efficiency and stringency, and different probes may require different conditions to achieve optimal hybridization. This embodiment also provides a method for selecting optimal conditions for specific probes. Once the probes are selected for specific target sequences, a test matrix can be made for selecting optimal buffer condition and temperature for each probe. In one example, the optimization procedure can be carried out as follows: the selected probe is prepared in a matrix of micro wells with different buffer contents. Hybridization can be performed with wells of the same buffer at various temperatures. Once optimal temperature is selected, different buffer compositions can be examined in sequential manner. Dehybridization buffer condition and temperature can also be investigated to assure complete removal of the probes after quantitation. Results can be analyzed for selecting best buffer and temperature condition for that specific probe. In one simple example, while one probe in the same hybridization buffer (e.g., 6×SSC, 6×SSPE) is prepared in a series of micro wells, different temperatures varying from 30–60° C. can be used in hybridization experiments for each individual well. The best hybridization temperature can be selected in this series from the hybridization results. Then another variable such as salt concentration, denaturing additives can be tested with optimized temperature. After the optimum hybridization condition is selected, the washing condition such as salt concentration, temperature is then selected in the same manner to provide desired stringency. This systematic selection procedure allows the optimal hybridization and dehybridization conditions for each probe to be quickly selected and stored in a database for future probe matrix synthesis.

c. Removal of Hybridized Probes

In this embodiment, the detected signal is based on the same label on different probes. In order to perform sequential analysis of different target sequences with probes of the same label, the hybridized probes must be removed before the next hybridization cycle can be carried out. This can be achieved by dehybridizing the probe from the target. The dehybridization step can be simply performed by elevating the temperature and/or by changing buffer conditions. The efficiency of the dehybridization can be monitored by the same detector used for analysis. Based on the hybridization kinetics, the hybridization probes will dissociate from the target almost irreversibly under denaturing conditions. To eliminate the effect of any residual fluorescence which may accumulate with the number of hybridization cycles, an additional step of photo bleaching is built into the process to destroy any fluorophores that are not dehybridized. In this way those residual hybridization probes are "silenced."

d. Sequential Analysis

Probe Matrix for Automated Quantitation

Hybridization probes used in this method are oligonucleotide sequences suspended in solution, which provides the highest hybridization efficiency and can be pre-distributed in a large number of wells fabricated into a glass block and arranged in a matrix. The volume of each well is small and the probe concentration is the same (μM–mM) in each well to simplify control for the robotic system and subsequent data analysis. In between these wells, three micro flow channels for the purpose of washing the micro-needle or the beads are fabricated to perform washing steps in hybridization, dehybridization, and optional photo bleaching (see FIG. 7 for an illustration). The temperature of each individual well can be controlled by a built-in Peltier's device and can be programmed individually for different temperatures between 1° C. and 80° C. Such probe matrices can be pre-fabricated for different set of genes, such as those involved in early development or hypertension disease or certain types of cancer. Such ready to use matrices can save the practitioner the trouble of designing and synthesizing the probes as well as the process of determining the exact conditions. A robotic arm is used to move the micro needle or the beads between the wells according to the designed routine. In the case of the micro needle, the needle can also have a shaking movement (e.g., driven by a piezo element) when inserted into the wells to improve the hydrodynamic performance. In the case of magnetic beads, a rotating magnetic field can be used to create movement of the beads in the wells. The matrix is driven by a stepper motor to align each column of the micro wells to the robotic arm and the detection device.

Since analysis of each probe is an independent experiment, any combination of probes can be selected for the matrix to suit analysis purpose. It is even possible for after production selection of probes used in analysis by simply performing analysis in selected wells. The flexibility of this design also allows instant changes of matrix composition in real time. As each probe is in its optimal hybridization buffer, each hybridization experiment can be carried out at optimal conditions to ensure maximum efficiency and specificity.

Extension Of Sequential Analysis with Parallel Detection

The method presented above is sequential analysis of each individual probe by a single wavelength detection. Although this is easiest, there is no fundamental difficulty in using multiple wavelength detection. When several different labels are used to label a set of probes, hybridization can be carried out in parallel if a set of probes is included in one well (i.e., several probes to different target genes with each labeled by a fluorophore of different wavelength). Even though hybridization will take slightly longer to complete with the increased sequence complexity in comparison to that of a single probe, it reaches saturation still in less than a minute for 4 or 5 probes, and the whole process will take shorter time in comparison to analyzing each one by one. For instance, oligonucleotide probes can be labeled with different fluorophors (e.g., FITC, Rhodamin, Cys-3, Cys-5, fluorescent nanocrystals with different emission wavelengths). When they are included in the same well, signal detection can be performed for each probe with wavelength selection after hybridization (see below). The measurement can also be carried out in parallel manner with mutlichannel signal collecting to speed up the process. A two-photon excitation system can be implemented for uniform excitation of the different fluorophores, therefore to ease the signal normalization process.

e. Stability of the Target Sequences

An important issue of this technology is whether the cDNA or mRNA can sustain the many hybridization/dehybridization cycles required for quantitation and the repeated illumination by the excitation wavelength. In traditional or array hybridization method, incubation is usually conducted at 50–60° C. for more than 24 hours without significant loss of nucleic acid materials. In this embodiment, hybridization condition can be optimized with lower temperature (30–50° C.) for each probe by adding denaturant (e.g., formamide) or quaternary ammonium salts (e.g., tetraethylammonium chloride (TEACl), tetramethylammonium chloride (TMACl)). Although this is not necessary, it can minimize the exposure of target sequences to harsh temperature conditions to prevent thermal degradation of the target sequences especially with limited number of copies. In the present embodiment, the time period for high-temperature exposure of the target sequences is actually shorter than the traditional and other array methods.

(4) Signal Detection

After the target sequences have hybridized with the specific probe, the amount of probe retained on the micro needle or the beads (i.e., hybridized to immobilized target sequences) can be accurately measured in order to yield the required information. As indicated earlier, different labels based on different physical principles can be used for this purpose.

Optical Detection

When fluorescenctly labeled probes are used in the hybridization assay, signal can be detected by a specially designed, high sensitivity, non-imaging fluorescence system. High sensitivity is important for low copy number detection. For example, for genes that are only expressed at 10 copies, there maybe only 6–8 labeled probes available for detection in practical terms. With 15 fluorophors attached to each probe, we only have 90–120 fluorophors to work with. For ordinary optics, 10% collection efficiency is considered fairly high. If we assume that 100,000 photons are available from each fluorophor, we have 900,000 photons.

Therefore, our detection system is specifically designed for this purpose. An example is shown in FIG. 8A. Here, the micro glass/quartz needle is illuminated from the back end coupled with an optic fiber from a laser or mercury/xenon sources (in case of IR for two-photon excitation, quartz will be used for the micro-needle). Since the dimension of the needle is greater than the wavelength of the excitation (for example, 488 nm), total internal reflection will guide most of light power to the end of the needle where the target sequences are attached. This needle is inserted into the small opening of the top concentrator, which reflects most of the emission into the PMT (photo multiplier tube) below, behind the filter used to select the signal. The PMT is normally operated in the photon counting mode, because we aim at low copy number detection. But the range of the PMT can be easily changed by an auto gain circuitry or programmed through a computer. In this configuration, nearly 100% of the fluorescence emission will be collected. A fast A to D (analog to digital) conversion is used to change the analog signal into a digital signal that is integrated or analyzed off line. It is noted that the quantum detection efficiency for a good PMT can be nearly 1. To minimize the influence of the illumination on the background, the PMT can be placed on the side (FIG. 8B). One skilled in the art would appreciate that other configurations can also be designed.

For multiple wavelength detection, an optical system will be needed to project the emission onto a diffraction grid in order to separate the different wavelength signals (FIG. 8C). Each probe signal will be detected with a separate PMT or a cooled CCD or a position sensitive sensor, and analyzed offline. An additional calibration procedure will be required for quantitation. In this case, additional filters may be used to reduce cross talk between different channels. To increase the excitation for all fluorophores, two photon excitation may be used. In this case, an IR laser may be used.

Mechanical Detection

In the case that small magnetic beads are used to tag the oligonucleotide probes as the label, a special atomic force microscope (AFM) like device can be used for sensing the force that can be generated on the magnetic beads by a controlled external magnetic field. The field can be designed to have a uniform gradient so that the force on each magnetic bead is uniform. After hybridization, the force is transferred from the magnetic beads on to the micro tip through the complimentary target sequences immobilized on the tip and then sensed by the cantilever to generate a signal. The total force generated by the magnetic beads is proportional to the number of beads hybridized to the target sequences, therefore the number of specific target sequence can be calculated.

(5) Mechanics of the Apparatus

As an example, a complete system for this analysis system and method thereof can be summarized as the following:

The system comprises three major sub-systems: target extraction and immobilization, sequential hybridization analysis, and data acquisition and analysis. All are computer controlled for automated operations (FIG. 9).

(1) Target Extraction and Immobilization

This component is a micromanipulating stage in a concealed chamber with humidity control. The device can be setup under any regular optical microscope for visualization of cell selection. The micropipette used for handling cell(s) and solution is moved along a series of micro wells to perform different procedures. The surface of micro wells is chemically treated to eliminate non-specific adsorption (e.g., siliconized). The temperature of individual well is controlled by a Peltier's device for different purposes. The micro wells are prefabricated with different buffer reagents and/or covalently linked sequences in a glass block, according to the requirement of different procedures. In the final step, a micro needle is mounted with micromanipulator to immobilize target sequences for analysis.

(II) Sequential Hybridization Analysis

The hybridization station is a computer controlled motion stage with an automated mechanical robot arm. It comprises a photo detection unit for fluorescence signal collection, a robot arm for moving target sequences, and a stage for holding the probe matrix block that can align the micro wells with the robot arm. After target sequences are immobilized on the micro needle, the probe is transferred into the hybridization station. The micro needle is mounted on a robotic arm and coupled to an optical fiber in the back. The probe matrix is made of micro wells arranged into a regular matrix with micro flow channels on the side. The micro wells are filled with selected hybridization probes in their optimal hybridization buffer. The micro flow channels can be used for washing and flushing with buffer. Target sequences on the micro needle are incubated with each specific probe in the micro well, and then is washed in the micro flow channel before hybridization detection. The optical fiber coupled to the micro needle is connected to a light source (laser, xenon/mercury etc.). The light transmitted into the micro needle and is guided to the end through total internal reflection, and illuminates the fluorophors on the hybridized probes, which are bound to the target sequences at the end of the micro needle. By illuminating the hybridized micro needle in the photo detection unit, fluorescence signals emitted from the hybridization probes are collected by a photo multiplier tube. The signals are converted into the digital form by a data acquisition board and stored in the computer system. Once the signal collection is completed, the micro needle is put back into micro flow channel for dehybridizing the probe from the target. Dehybridization can be achieved by changing buffer and/or by elevating temperature. An additional step of photo bleaching can be performed in another micro flow channel if necessary. After one hybridization cycle, the robot arm moves the micro needle in to the next micro well to start another round of measurement. The stage is automated and controlled by a computer system to align micro wells with the robot arm. The robot arm, which is also controlled by a computer, moves micro needle between micro wells, flow channels and the optical detection unit.

(III) Computer Interface, Data Acquisition and Analysis

An integrated software system is designed to realize the automation of the analysis, robot movement, optical detection, data acquisition, and the humidity and temperature control of individual chamber and micro wells. Hybridization results are captured, normalized and then stored in the database. The analytical capability of the system can also be expanded by parallel processing of several analysis stations that have different probe matrices.

(6) Analyzing the Entire Genome

As indicated earlier, this embodiment also provides a method to duplicate the original target material for a limited, up to 30 times (Since each round of synthesis takes a couple of hours to complete, which limits the number of rounds that can be performed in practical terms). Therefore, the total mRNA from a single cell can be analyzed by 30 machines in parallel, containing different probe matrices. With parallel processing of 30 analysis stations (with single wavelength detection), the genes that can be analyzed are up to 45,000 in 24 hours without sacrificing the sensitivity of the analysis. With multiple wavelength detection, this is increased to 135,000~180,000. The entire process should take no more than 3 days. Since the process of the array technology still takes a few days for 100,000 genes, the current invention is therefore comparable to the array technology, but require only small number of cells or single cell to perform the full genome analysis. It is contemplated that such analysis will be able to provide critical information that can not be obtained by any other technique currently available.

(7) Examples of Applications

Cancer

The genes expressed in cancer cells can be analyzed. This is particularly useful when the sample is small, such as obtained through biopsy. When specific genes and their products are identified for specific types of cancers, this technique will provide a reliable diagnosis tool in clinical medicine with only the collection of a few cells from subjects. This method would be free from human error. A very important application is to analyze the genes expressed in the early stages of cancer, at which the available material is too small for any other analytical approach. It is possible that there may be significant differences between the early stage cancer cells and that of mature tumors. A systematic study of different cancer cells may allow the identification of "universal" targets that transcends different cell types. If such targets can be found, they would serve as the most effective target for the development of anti-cancer drugs. Such drugs may convey a "universal" control of all cancers or a group of cancers in the human body when administered. It is also considerable interest to understand the difference between those cells adjacent to tumors than those normal cells. If these cells can provide identifiable targets, they may help the delivery of anti-cancer drugs as well.

Developmental Biology

One of the most difficult subjects in biology is to understand how a fertilized egg is developed into an embryo and into a whole animal. A key to this question is to understand the different set of genes that are "turned on" at the onset of differentiation. In other words, we wish to know what genes are first expressed in the first "arm" cell, for example. This method allows us to select one or a few cells from a single embryo going through differentiation at various stages and to analyze the genes expressed in these cells. A systematic study of the embryo over the entire developmental process may provide a road map of the genes or group of genes that are turned on and off at various time and places (on the embryo). With the completion of the sequencing of the entire human genome, this task becomes particularly important and approachable. Such a road map will ultimately uncover the mystery how an animal is coming into being.

These are just two important applications of this technology. Applications in many other areas, such as the analysis of the key genes that control the cell cycle progression without the need for synchronization, are also contemplated. In many ways, this technology provides a unique opportunity to look into the inner workings of living systems, which is made particularly relevant at this post genomic era.

E. EXAMPLES

Single-Stranded DNA Stability Test

One example is shown in FIG. 10. In this experiment, single stranded DNA samples that have copy numbers equivalent to the total mRNA material from 50 cells (50 pg)

or 5 cell (5 pg) were used to test the stability of the target sequences when applied to the sequential hybridization reactions. Both 50 pg and 5 pg of a synthetic ss-DNA (2 kbp) were put through various numbers (50, 100, 200, 500) of temperature cycles (42° C. 30 s, 65° C. 10 s, 25° C. 30 s) in the hybridization buffer. The amount of the remaining ss-DNA in those samples were analyzed, using the quantitative PCR (QPCR) method. The plot shows that the ss-DNA were not significantly degraded after 500 cycles.

Exemplary Hybridization Reaction

FIG. 6 shows an exemplary hybridization reaction. In this experiment, oligo-dT coated-beads are incubated in hybridization buffer (10 mM Tris-HCl, 1 mM EDTA, 1 M NaCl, pH=7.5) with single stranded DNA containing oligo-dA sequence. The hybridization reaction is monitored by measuring the single stranded DNA remained in solution at different time points. An aliquot of remaining unhybridized DNA is taken for quantitative PCR reaction. The PCR reaction is normalized by using a known concentration of single stranded DNA as the standard. In this plot, the x-axis is time (second), and the y-axis is the fraction of initial single stranded DNA remained in solution. The initial concentration of oligo-dT sequence is calculated as the following: the number of total oligo-dT is $9 \times 10^{10}$, the reaction is carried out in 10 µl, so the effective concentration is 15 nM. Single stranded DNA is added at 40 pM. The hybridization reaction is a first order reaction, so the rate constant resulted from fitting the data is $1.7 \times 10^5$.

F. REFERENCES

1. U.S. Pat. No. 5,665,540, entitled "Multicolor in situ hybridization methods for genetic testing:'
2. U.S. Pat. No. 4,888,278, entitled "In-situ hybridization to detect nucleic acid sequences in morphologically intact cells;"
3. U.S. Pat. No. 6,046,006, entitled "Sequential hybridization of fungal cell DNA and method for the detection of fungal cells in clinical material;"
4. U.S. Pat. No. 6,410,229, entitled "Expression monitoring by hybridization to high density nucleic acid arrays;"
5. U.S. Pat. No. 6,344,316, entitled "Nucleic acid analysis techniques;"
6. U.S. Pat. No. 6,379,898, entitled "Nucleic acid detection;"
7. U.S. Pat. No. 6,403,957, entitled "Nucleic acid reading and analysis system;"
8. U.S. Pat. No. 6,376,177, entitled "Apparatus and method for the analysis of nucleic acids hybridization on high density NA chips;"
9. U.S. Pat. No. 6,210,932, entitled "System for detecting nucleic acid hybridization, preparation method and application thereof;"
10. U.S. Pat. No. 6,344,316, entitled "Nucleic acid analysis techniques;"
11. U.S. Pat. No. 6,309,824, entitled "Methods for analyzing a target nucleic acid using immobilized heterogeneous mixtures of oligonucleotide probes;"
12. U.S. Pat. No. 6,200,752, entitled "Method and composition for detecting the presence of a nucleic acid sequence in a sample;"
13. U.S. Pat. No. 6,355,429, entitled "Devices and methods for optical detection of nucleic acid hybridization;"
14. U.S. Pat. No. 5,514,545, entitled "Method for characterizing single cells based on RNA amplification for diagnostics and therapeutics;"
15. U.S. Pat. No. 6,235,483, entitled "Methods and kits for indirect labeling of nucleic acids;"
16. U.S. Pat. No. 6,228,580, entitled "Nucleic acid detection method using nucleotide probes enabling both specific capture and detection;"
17. U.S. Pat. No. 4,542,102, entitled "Coupling of nucleic acids to solid;"
18. U.S. Pat. No. 4,588,682, entitled "Binding nucleic acid to a support;"
19. U.S. Pat. No. 5,215,882, entitled "Method of immobilizing nucleic acid on a solid surface for use in nucleic acid hybridization assays;"
20. U.S. Pat. No. 5,780,227, entitled "Oligonucleotide probe conjugated to a purified hydrophilic alkaline;"
21. U.S. Pat. No. 5,759,777, entitled "Hybridization promotion reagents;"
22. U.S. Pat. No. 5,728,527, entitled "Detection of hybridized oligonocleotide probes in living cells;"
23. U.S. Pat. No. 5,589,335, entitled "Hybridization promotion reagents;"
24. U.S. Pat. No. 5,853,986, entitled "Chemical promotion of nucleic acid hybridization;"
25. U.S. Pat. No. 4,787,963, entitled "Method and means for annealing complementary nucleic acid molecules at an accelerated rate;"
26. U.S. Pat. No. 4,670,380, entitled "Assays utilizing labeled nucleic acid probes;"
27. Amasino, R. M. (1986). Acceleration of nucleic acid hybridization rate by polyethylene glycol, Anal Biochem 152, 304–7;
28. Casey, J., and Davidson, N. (1977). Rates of formation and thermal stabilities of RNA:DNA and DNA:DNA duplexes at high concentrations of formamide, Nucleic Acids Res 4, 1539–52;
29. Chang, C. T., Hain, T. C., Hutton, J. R., and Wetmur, J. G. (1974). Effects of microscopic and macroscopic viscosity on the rate of renaturation of DNA, Biopolymers 13, 1847–58;
30. Flavell, R. A., Birfelder, E. J., Sanders, J. P., and Borst, P. (1974). DNA-DNA hybridization on nitrocellulose filters. 1. General considerations and non-ideal kinetics, Eur J Biochem 47, 535–43;
31. Forster, A. C., McInnes, J. L., Skingle, D. C., and Symons, R. H. (1985). Non-radioactive hybridization probes prepared by the chemical labelling of DNA and RNA with a novel reagent, photobiotin, Nucleic Acids Res 13, 745–61;
32. Hames B. D. and S. J. Higgins, "Nucleic Acid Hybridization: A practical Approach" (1985) IRL Press, Oxford;
33. Hoeltke, H. J., Ettl, I., Finken, M., West, S., and Kunz, W. (1992). Multiple nucleic acid labeling and rainbow detection, Anal Biochem 207, 24–31;
34. Hutton, J. R. (1977). Renaturation kinetics and thermal stability of DNA in aqueous solutions of formamide and urea, Nucleic Acids Res 4, 3537–55;
35. Jacobs, K. A., Rudersdorf, R., Neill, S. D., Dougherty, J. P., Brown, E. L., and Fritsch, E. F. (1988). The thermal stability of oligonucleotide duplexes is sequence independent in tetraalkylammonium salt solutions: application to identifying recombinant DNA clones, Nucleic Acids Res 16, 4637–50;
36. Langer, P. R., Waldrop, A. A., and Ward, D. C. (1981). Enzymatic synthesis of biotin-labeled polynucleotides: novel nucleic acid affinity probes, Proc Natl Acad Sci USA 78, 6633–7;

37. Leitch, A. R., Schwarzacher, T., Jackson, D. and Leitch, I. J., "In situ hybridization" (eds) (1994) BIOS Scientific Publishers, Oxford;
38. Maskos, U., and Southern, E. M. (1992). Oligonuclcotide hybridizations on glass supports: a novel linker for oligonucleotide synthesis and hybridization properties of oligonucleotides synthesised in situ, Nucleic Acids Res 20, 1679–84;
39. Renz, M., and Kurz, C. (1984). A colorimetric method for DNA hybridization, Nucleic Acids Res 12, 3435–44;
40. Sambrook, Fritisch, and Maniatis., "Molecular cloning—A laboratory Mannual", second edition, Cold Spring Harbor Laboratory Press, Cold Spring Harbor, N.Y.;
41. Southern, E. M. (1975). Detection of specific sequences among DNA fragments separated by gel electrophoresis, J Mol Biol 98, 503–17;
42. Wahl, G. M., Stem, M., and Stark, G. R. (1979). Efficient transfer of large DNA fragments from agarose gels to diazobenzyloxymethyl-paper and rapid hybridization by using dextran sulfate, Proc Natl Acad Sci USA 76, 3683–7;
43. Wetmur, J. G., and Davidson, N. (1968). Kinetics of renaturation of DNA, J Mol Biol 31, 349–70; and
44. Wood, W. I., Gitschier, J., Lasky, L. A., and Lawn, R. M. (1985). Base composition-independent hybridization in tetramethylammonium chloride: a method for oligonucleotide screening of highly complex gene libraries, Proc Natl Acad Sci USA 82, 1585–8.

The above examples are included for illustrative purposes only and are not intended to limit the scope of the invention. Many variations to those described above are possible. Examples of these variations include, but not limited to, the substrate materials for making the chips, the electrode structures for generating electric fields, the structure of electromagnetic units for producing magnetic fields, the structures of piezoelectric elements for producing acoustic fields, the structures of optical elements for generating optical fields, the structures of heating/cooling elements for generating temperature gradient, etc. Since modifications and variations to the examples described above will be apparent to those of skill in this art, it is intended that this invention be limited only by the scope of the appended claims.

The invention claimed is:
1. A method for analyzing gene expression profiles of a cell, which method comprises:
  a) providing isolated mRNA or cDNA target sequences from a cell, wherein the mRNA or cDNA sequences are unknown;
  b) directly immobilizing the mRNA or cDNA sequences on the surface of a microneedle, whereby the immobilization is via covalent binding, via non-covalent binding, via an interaction with an oligo-dT or oligo-dA that is covalently bound to the microneedle, via an interaction with an oligo-dT or oligo-dA that is covalently bound to the microneedle via a flexible spacer; via a flexible spacer; via crosslinking the immobilized mRNA or cDNA sequences to an oligo-dT or oligo-dA; or via crosslinking the immobilized mRNA or cDNA sequences to the microneedle;
  c) sequentially hybridizing in two or more cycles of hybridization said isolated mRNA or cDNA target sequences with a plurality of nucleotide probes, wherein the sequences of the probes are known and wherein each of the probes is in solution; and
  d) assessing the sequential hybridization between said isolated mRNA or cDNA target sequences and said plurality of nucleotide probes to analyze the expression profile of at least one gene of said cell.

2. The method of claim 1, wherein the isolated mRNA target sequences from a cell are provided for and hybridized with a plurality of nucleotide probes.

3. The method of claim 1, wherein the isolated cDNA target sequences from a cell are provided for and hybridized with a plurality of nucleotide probes.

4. The method of claim 3, wherein the isolated cDNA target sequences are complementary to the mRNA target sequences.

5. The method of claim 3, wherein the isolated cDNA target sequences have the same polarity as the mRNA target sequences.

6. The method of claim 1, wherein a combination of the isolated mRNA and cDNA target sequences from a cell are provided for and hybridized with a plurality of nucleotide probes.

7. The method of claim 1, wherein the mRNA target sequences are extracted from a cell with biochemical, cell biological or biophysical means.

8. The method of claim 1, wherein the mRNA target sequences are extracted from a cell by a micromanipulator controlled micropipette, adsorption on surface of microwells, extraction with oligo-dT or capillary electrophoresis.

9. The method of claim 1, further comprising synthesizing first strand cDNA target sequences complementary to the extracted mRNA target sequences.

10. The method of claim 9, further comprising synthesizing second strand cDNA target sequences complementary to the first strand cDNA target sequences.

11. The method of claim 10, wherein the mRNA target sequences and the first strand cDNA target sequences are degraded or removed from the second strand cDNA target sequences and the second strand cDNA target sequences alone are used in the hybridization with the nucleotide probes.

12. The method of claim 10, wherein multiple copies of the second strand cDNA target sequences are synthesized.

13. The method of claim 1, further comprising removing uninteresting mRNA or cDNA sequences from the mRNA or cDNA target sequences prior to the hybridization between the mRNA or cDNA target sequences and the nucleotide probes.

14. The method of claim 13, wherein the uninterested mRNA or cDNA sequences are removed from the mRNA or cDNA target sequences using immobilized nucleic acid sequences that are complimentary to the uninteresting mRNA or cDNA sequences to remove them from the sample and leaving them behind while the rest of the sample is subsequently transferred away.

15. The method of claim 1, further comprising removing abundant or intermediate abundant class of mRNA or cDNA sequences from low abundant class of mRNA or cDNA target sequences prior to the hybridization between the low abundant class of mRNA or cDNA target sequences and the nucleotide probes.

16. The method of claim 1, wherein the isolated mRNA or cDNA target sequences are immobilized to a surface suitable for hybridization analysis prior to the hybridization between the mRNA or cDNA target sequences and the nucleotide probes.

17. The method of claim 1, wherein the microneedle is fabricated from glass, quartz or plastic.

18. The method of claim 16, wherein the isolated mRNA or cDNA target sequences are immobilized to a small area of the surface less than about 10% of the total surface area and the remaining surface area is treated to prevent non-specific attachment of the mRNA or cDNA target sequences.

19. The method of claim 16, wherein the isolated mRNA or cDNA target sequences are immobilized to the surface of the apex of the microneedle and the remaining surface area is treated to prevent non-specific association of the isolated mRNA or cDNA target sequences.

20. The method of claim 16, wherein the isolated mRNA or cDNA target sequences are immobilized to a surface area ranging from about 1 micron to about 10 millimeters.

21. The method of claim 16, wherein the isolated mRNA or cDNA target sequences are immobilized to the surface via covalent and/or non-covalent binding.

22. The method of claim 16, wherein the isolated mRNA or cDNA target sequences are immobilized to the surface via an interaction with oligo-dT or oligo-dA that is covalently bound to the surface.

23. The method of claim 22, wherein the oligo-dT or oligo-dA is covalently bound to the surface through a flexible spacer or directly.

24. The method of claim 22, further comprising crosslinking the immobilized mRNA or cDNA target sequences to the oligo-dT or oligo-dA.

25. The method of claim 24, wherein the crosslinking reaction is activated by photolysis or chemical cleavage.

26. The method of claim 1, further comprising linearly amplifying the mRNA or cDNA target sequences prior to the hybridization between the mRNA or cDNA target sequences and the nucleotide probes.

27. The method of claim 26, wherein the cDNA target sequences are linearly amplified via transcription using the cDNA target sequences as the template.

28. The method of claim 26, wherein the first strand cDNA target sequences are linearly amplified via synthesizing multiple copies of second strand cDNA target sequences using the first strand cDNA target sequences as the template.

29. The method of claim 26, wherein the mRNA or cDNA target sequences are linearly amplified from about 10 to about 100 fold.

30. The method of claim 26, further comprising immobilizing the linearly amplified mRNA or cDNA target sequences to a surface suitable for hybridization analysis prior to the hybridization between the amplified mRNA or cDNA target sequences and the nucleotide probes.

31. The method of claim 1, wherein the nucleotide probes have from about 15 to about 100 nucleotides.

32. The method of claim 1, wherein the nucleotide probes comprise a detectable label.

33. The method of claim 32, wherein the detectable label can be detected by optical, magnetic, mechanic, spectroscopic, photochemical, biochemical, immunochemical, radioactive or enzymatic means.

34. The method of claim 32, wherein the detectable label is a fluorescent or magnetic moiety.

35. The method of claim 32, wherein the nucleotide probes are uniformly labeled.

36. The method of claim 1, which is sensitive enough to detect the presence of a single probe.

37. The method of claim 1, wherein the nucleotide probes are specific or degenerate probes.

38. The method of claim 1, wherein the nucleotide probes have similar hybridization or dehybridization efficiency.

39. The method of claim 1, wherein the nucleotide probes comprise a normalization probe.

40. The method of claim 1, wherein same or different probes are used in different cycles of the sequential hybridization reactions.

41. The method of claim 1, further comprising assessing expression of an abundant gene as an expression level normalization control.

42. The method of claim 1, wherein in at least one of the sequential hybridization reactions, the nucleotide probes are in excess relative to the amount of the mRNA or cDNA target sequences so that the hybridization reaction is a first order reaction or a saturation hybridization.

43. The method of claim 1, wherein in all the sequential hybridization reactions, the nucleotide probes are in excess relative to the amount of the mRNA or cDNA target sequences so that the hybridization reaction is a first order reaction and a saturation hybridization.

44. The method of claim 1, wherein the molar ratio of the nucleotide probes over the mRNA or cDNA target sequences is about at least 1,000:1.

45. The method of claim 1, wherein the hybridization buffer comprises an agent to lower the hybridization temperature, an agent to reduce degradation of the mRNA or cDNA target sequences, or an agent to retain the pH at range from about 6.5 to about 7.5.

46. The method of claim 1, further comprising removing residual detectable signal from a proceeding hybridization reaction before the next hybridization reaction.

47. The method of claim 46, wherein residual fluorescent signal from a proceeding hybridization reaction is removed by photo bleaching before the next hybridization reaction.

48. The method of claim 1, wherein at least one of the sequential hybridization reactions is conducted at a temperature ranging from about 30° C. to about 60° C. in the presence of a denaturant or a quaternary ammonium salt.

49. The method of claim 1, wherein at least 100 different isolated mRNA or cDNA target sequences are provided for and hybridized to the nucleotide probes.

50. The method of claim 1, wherein the isolated mRNA or cDNA target sequences comprise the entire population of cellular mRNA or corresponding cDNA from a cell.

51. The method of claim 1, wherein the isolated mRNA or cDNA target sequences from a single cell are provided for and hybridized to the nucleotide probes.

52. The method of claim 1, wherein the isolated mRNA or cDNA target sequences from less than 1,000 cells are provided for and hybridized to the nucleotide probes.

53. The method of claim 1, wherein the same isolated mRNA or cDNA target sequences are sequentially hybridized to 10 different nucleotide probes.

54. The method of claim 1, wherein the same isolated mRNA or cDNA target sequences are sequentially hybridized to about 1,500 different nucleotide probes within 24 hours.

55. The method of claim 1, wherein the isolated mRNA or cDNA target sequences are hybridized to multiple probes with different labels for detecting multiple target sequences in one hybridization.

56. The method of claim 1, wherein the isolated mRNA or cDNA target sequences are involved in a biological pathway, encode a group of proteins with identical or similar biological function, expressed in a stage of cell cycle, expressed in a cell type, expressed in a tissue type, expressed in an organ type, expressed in a developmental stage, encode a group of proteins whose expressions and/or activities are altered in a disease or disorder type or stage, or encode a group of proteins whose expressions and/or activities are altered by drug or other treatments.

57. The method of claim 56, wherein the disease or disorder is selected from the group consisting of neoplasm, an immune system disease or disorder, a metabolism disease or disorder, a muscle and bone disease or disorder, a nervous system disease or disorder, a transporter disease or disorder, a signal disease or disorder and an infection.

58. The method of claim 1, wherein the cell is selected from the group consisting of an animal cell, a plant cell, a fungus cell, a bacterium cell, a recombinant cell and a cultured cell.

59. The method of claim 1, wherein the cell is derived from a tissue or biopsy sample.

60. The method of claim 1, wherein the number of probes is not predetermined before the sequential hybridization and the number of probes is adjusted according to the sequential hybridization reaction(s) that has already been performed.

61. The method of claim 1, wherein after a number of sequential hybridization reaction(s) is performed, the mRNA or cDNA target sequences are stored for a time and then re-analyzed with a further hybridization reaction.

62. The method of claim 1, wherein the mRNA or cDNA target sequences are subjected to parallel sequential hybridization reactions.

63. The method of claim 62, wherein in at least one of the parallel sequential hybridization reactions, the isolated mRNA or cDNA target sequences are hybridized to multiple probes with different labels for detecting multiple target sequences in one hybridization.

64. The method of claim 1, wherein in at least one of the sequential hybridization reactions, the hybridization condition is individually adjusted.

65. A method for analyzing gene expression profiles of a cell, which method comprises:

a) providing isolated mRNA or cDNA target sequences from a cell, wherein the mRNA or cDNA sequences are unknown;

b) directly immobilizing the mRNA or cDNA sequences on the surface of a microneedle, whereby the immobilization is via covalent binding, via non-covalent binding, via an interaction with an oligo-dT or oligo-dA that is covalently bound to the microneedle, via an interaction with an oligo-dT or oligo-dA that is covalently bound to the microneedle via a flexible spacer; via a flexible spacer; via crosslinking the immobilized mRNA or cDNA sequences to an oligo-dT or oligo-dA; or via crosslinking the immobilized mRNA or cDNA sequences to the microneedle;

c) sequentially hybridizing in two or more cycles of hybridization said isolated mRNA or cDNA target sequences with a plurality of nucleotide probes, wherein the sequences of the probes are known and wherein each of the probes is in solution;

d) dehybridizing between at least two of the cycles; and e) assessing the sequential hybridization between said isolated mRNA or cDNA target sequences and said plurality of nucleotide probes to analyze the expression profile of at least one gene of said cell.

66. The method of claim 65, wherein the dehybridization between at least two of the cycles is effected via elevated temperature or changed solution conditions.

67. The method of claim 1, wherein the microneedle is a microprobe.

* * * * *